United States Patent
Yamashita et al.

(10) Patent No.: US 12,195,559 B2
(45) Date of Patent: Jan. 14, 2025

(54) CDCA1-DERIVED PEPTIDE AND VACCINE CONTAINING SAME

(71) Applicant: ONCOTHERAPY SCIENCE, INC., Kawasaki (JP)

(72) Inventors: Sachiko Yamashita, Kawasaki (JP); Tetsuro Hikichi, Kawasaki (JP)

(73) Assignee: ONCOTHERAPY SCIENCE, INC., Kawasaki (JP)

( * ) Notice: Subject to any disclaimer, the term of this patent is extended or adjusted under 35 U.S.C. 154(b) by 0 days.

(21) Appl. No.: 18/094,167

(22) Filed: Jan. 6, 2023

(65) Prior Publication Data

US 2023/0159588 A1   May 25, 2023

Related U.S. Application Data

(63) Continuation of application No. 17/264,277, filed as application No. PCT/JP2019/030117 on Aug. 1, 2019, now abandoned.

(30) Foreign Application Priority Data

Aug. 2, 2018 (JP) ................. 2018-145607

(51) Int. Cl.
| C07K 7/06 | (2006.01) |
| A61K 35/15 | (2015.01) |
| A61K 35/17 | (2015.01) |
| A61K 39/00 | (2006.01) |
| A61P 35/00 | (2006.01) |
| C07K 14/74 | (2006.01) |
| C12N 5/0784 | (2010.01) |
| A61K 38/00 | (2006.01) |

(52) U.S. Cl.
CPC ............... *C07K 7/06* (2013.01); *A61K 35/15* (2013.01); *A61K 35/17* (2013.01); *A61K 39/00* (2013.01); *A61K 39/001149* (2018.08); *A61K 39/4611* (2023.05); *A61K 39/4615* (2023.05); *A61K 39/4622* (2023.05); *A61K 39/464449* (2023.05); *A61P 35/00* (2018.01); *C07K 14/70539* (2013.01); *C12N 5/0639* (2013.01); *A61K 38/00* (2013.01)

(58) Field of Classification Search
None
See application file for complete search history.

(56) References Cited

U.S. PATENT DOCUMENTS

| 6,573,243 | B1 | 6/2003 | Itagaki et al. |
| 6,699,703 | B1 | 3/2004 | Doucette-Stamm et al. |
| 6,858,204 | B2 | 2/2005 | Henderson et al. |
| 7,214,786 | B2 | 5/2007 | Kovalic et al. |
| 7,776,341 | B2 | 8/2010 | Belisle et al. |
| 7,943,295 | B2 | 5/2011 | Nakamura et al. |
| 8,598,125 | B2 | 12/2013 | Nishimura et al. |
| 9,387,238 | B2 | 7/2016 | Tsunoda et al. |
| 9,687,538 | B2 | 6/2017 | Nishimura et al. |
| 10,206,989 | B2 | 2/2019 | Nishimura et al. |
| 10,576,102 | B2 | 3/2020 | Tsunoda et al. |
| 10,676,508 | B2 | 6/2020 | Yamashita et al. |
| 10,676,514 | B2 | 6/2020 | Tsunoda et al. |
| 10,711,047 | B2 | 7/2020 | Tsunoda et al. |
| 11,242,365 | B2 | 2/2022 | Yamashita et al. |
| 2003/0165513 | A1 | 9/2003 | Ramakrishna et al. |
| 2006/0088527 | A1 | 4/2006 | Henderson et al. |
| 2006/0216301 | A1 | 9/2006 | Tahara et al. |
| 2007/0053922 | A1 | 3/2007 | Sette et al. |
| 2011/0229524 | A1 | 9/2011 | Fritsche et al. |
| 2011/0263012 | A1 | 10/2011 | Nakamura et al. |
| 2014/0147432 | A1 | 5/2014 | Bancel et al. |
| 2017/0333476 | A1* | 11/2017 | Tsunoda ................. A61P 35/00 |
| 2018/0079791 | A1 | 3/2018 | Tsunoda et al. |
| 2018/0346512 | A1 | 12/2018 | Yamashita et al. |

FOREIGN PATENT DOCUMENTS

| CN | 1357006 A | 7/2002 |
| JP | 2004512824 A | 4/2004 |
| JP | 2011524737 A | 9/2011 |
| JP | 2015529629 A | 10/2015 |

(Continued)

OTHER PUBLICATIONS

"Database Printout: Database IBIS GSP, AAG74867", Integrated Biotechnological Information Services, Sep. 3, 2001, pp. 1-2.

(Continued)

*Primary Examiner* — Ronald T Niebauer
(74) *Attorney, Agent, or Firm* — Kilpatrick Townsend & Stockton LLP

(57) ABSTRACT

The present invention provides CDCA1-derived epitope peptides having the ability to induce cytotoxic T cells. The present invention further provides polynucleotides encoding the peptides, antigen-presenting cells presenting the peptides, and cytotoxic T cells targeting the peptides, as well as methods of inducing the antigen-presenting cells or CTLs. The present invention also provides compositions and pharmaceutical compositions containing them as an active ingredient. Further, the present invention provides methods of treating and/or preventing cancer, and/or preventing postoperative recurrence thereof, using the peptides, polynucleotides, antigen-presenting cells, cytotoxic T cells or pharmaceutical compositions of the present invention. Methods of inducing an immune response against cancer are also provided.

10 Claims, 3 Drawing Sheets

Specification includes a Sequence Listing.

(56) References Cited

FOREIGN PATENT DOCUMENTS

| | | |
|---|---|---|
| RU | 2560431 C2 | 8/2015 |
| WO | 200078806 A1 | 12/2000 |
| WO | 200122920 A2 | 4/2001 |
| WO | 200204514 A2 | 1/2002 |
| WO | 2002094981 A2 | 11/2002 |
| WO | 2003025010 A2 | 3/2003 |
| WO | 2003037267 A2 | 5/2003 |
| WO | 2004024766 A2 | 3/2004 |
| WO | 2004031413 A2 | 4/2004 |
| WO | 2004067023 A2 | 8/2004 |
| WO | 2004080148 A2 | 9/2004 |
| WO | 2005016962 A2 | 2/2005 |
| WO | 2005028676 A2 | 3/2005 |
| WO | 2005089735 A2 | 9/2005 |
| WO | 2006085684 A2 | 8/2006 |
| WO | 2007013480 A2 | 2/2007 |
| WO | 2007013665 A2 | 2/2007 |
| WO | 2007013671 A2 | 2/2007 |
| WO | 2009025117 A1 | 2/2009 |
| WO | 2009153992 A1 | 12/2009 |
| WO | 2010037395 A2 | 4/2010 |
| WO | 2010/095428 A1 | 8/2010 |
| WO | 2014010229 A1 | 1/2014 |
| WO | 2016021506 A1 | 2/2016 |
| WO | 2016021508 A1 | 2/2016 |
| WO | 2017026503 A1 | 2/2017 |
| WO | 2017061523 A1 | 4/2017 |

OTHER PUBLICATIONS

"Mannide Monooleate", Biosynth, Available Online at: https://www.biosynth.com/p/MM30170/9049-98-3-mannide-monooleate, 2022.
"Mineral Oils, Untreated or Mildly Treated", NCBI Bookshelf, 2022, 15 pages.
"Sequence 166 from U.S. Pat. No. 6,867,283", Database Genbank: AAY06266.1, Apr. 2005, 1 page.
U.S. Appl. No. 17/264,277 , Final Office Action, Mailed On Oct. 7, 2022, 23 pages.
U.S. Appl. No. 17/264,277 , Non-Final Office Action, Mailed On May 12, 2022, 23 pages.
Adams et al., "Prediction of Binding to MHC Class 1 Molecules", Journal of Immunological Methods, vol. 185, No. 2, Sep. 25, 1995, pp. 181-190.
Anderson , "Human Gene Therapy", Nature, vol. 392, Apr. 30, 1998, pp. 25-30.
Belli et al., "Vaccination of Metastatic Melanoma Patients With Autologous Tumor-Derived Heat Shock Protein gp96-Peptide Complexes: Clinical and Immunologic Findings", Journal of Clinical Oncology, vol. 20, No. 20, Oct. 15, 2002, pp. 4169-4180.
Berger et al., "Circulation and Homing of Melanoma-Reactive T Cells to Both Cutaneous and Visceral Metastases After Vaccination With Monocyte-Derived Dendritic Cells", International Journal of Cancer, vol. 111, No. 2, Aug. 20, 2004, pp. 229-237.
Bodey et al., "Failure of Cancer Vaccines: The Significant Limitations of this Approach to Immunotherapy", Anticancer Research, vol. 20, No. 4, Jul. 1, 2000, pp. 2665-2674.
Boon et al., "Human T Cell Responses Against Melanoma", Annual Review of Immunology, vol. 24, Apr. 2006, pp. 175-208.
Boon et al., "Human Tumor Antigens Recognized by T Lymphocytes", Journal of Experimental Medicine, vol. 183, No. 3, Mar. 1996, pp. 725-729.
Boon , "Tumor Antigens Recognized by Cytolytic T Lymphocytes: Present Perspectives for Specific Immunotherapy", International Journal of Cancer, vol. 54, No. 2, May 8, 1993, pp. 177-180.
Bork , "Powers and Pitfalls in Sequence Analysis: The 70% Hurdle", Genome Research, vol. 10, No. 4, Apr. 2000, pp. 398-400.
Butterfield et al., "Generation of Human T-Cell Responses to an HLA-A2.1-Restricted Peptide Epitope Derived From α-Fetoprotein", Cancer Research, vol. 59, No. 13, Jul. 1, 1999, pp. 3134-3142.

Cao et al., "Analysis of the Frequencies of HLA-A, B, and C Alleles and Haplotypes in the Five Major Ethnic Groups of the United States Reveals High Levels of Diversity in these Loci and Contrasting Distribution Patterns in these Populations", Human Immunology, vol. 62, No. 9, Sep. 2001, pp. 1009-1030.
Celis , "Getting Peptide Vaccines to Work: Just a Matter of Quality Control?", Journal of Clinical Investigation, vol. 110, No. 12, Dec. 15, 2002, pp. 1765-1768.
Celis et al., "Identification of Potential CTL Epitopes of Tumor-Associated Antigen MAGE-1 for Five Common HLA-A Alleles", Molecular Immunology, vol. 31, No. 18, Dec. 1994, pp. 1423-1430.
Chujoh et al., "The Role of Anchor Residues in the Binding of Peptides to HLA-A 1101 Molecules", Tissue Antigens, vol. 52, No. 6, Dec. 1998, pp. 501-509.
Coulie et al., "Cytolytic T-cell Responses of Cancer Patients Vaccinated With a MAGE Antigen", Immunological Reviews, vol. 188, Oct. 2002, pp. 33-42.
Crystal , "Transfer of Genes to Humans: Early Lessons and Obstacles to Success", Science, vol. 270, No. 5235, Oct. 20, 1995, pp. 404-410.
Dermer , "Another Anniversary for the War on Cancer", Biotechnology, vol. 12, Mar. 1994, p. 320.
Dionne et al., "Functional Characterization of CTL Against gp100 Altered Peptide Ligands", Cancer Immunology, Immunotherapy, vol. 52, No. 4, Feb. 18, 2003, pp. 199-206.
Dionne et al., "Her-2/Neu Altered Peptide Ligand-Induced CTL Responses: Implications for Peptides With Increased HLA Affinity and T-Cell-Receptor Interaction", Cancer Immunology Immunotherapy, vol. 53, No. 4, Apr. 2004, pp. 307-314.
Doerks et al., "Protein Annotation: Detective Work for Function Prediction", Trends in Genetics, vol. 14, No. 6, Jun. 1998, pp. 248-250.
Eck et al., "Gene-Based Therapy", The Pharmacological Basis of Therapeutics, Goodman and Gilman, Ninth Edition, 1996, pp. 77-101.
Engelhard , "Structure of Peptides Associated With MHC Class I Molecules", Current Opinion in Immunology vol. 6, No. 1, Feb. 1994, pp. 13-23.
Ezzell et al., "Cancer "Vaccines": An Idea Whose Time Has Come?", Journal of NIH Research, vol. 7, Jan. 1995, pp. 46-49.
Falk et al., "Allele-Specific Motifs Revealed by Sequencing of Self-Peptides Eluted from MHC Molecules", Nature, vol. 351, No. 6324, May 23, 1991, pp. 290-296.
Falk et al., "Peptide Motifs of HLA-A1, -A11, -A31, and -A33 Molecules", Immunogenetics, vol. 40, No. 3, 1994, pp. 238-241.
Fournier et al., "Randomized Clinical Studies of Anti-Tumor Vaccination: State of the Art in 2008", Expert Review of Vaccines, vol. 8, No. 1, Jan. 2009, pp. 51-66.
Freshney , "Culture of Animal Cells", A Manual of Basic Technique, 1983, 4 pages.
Fujie et al., "A MAGE-1-Encoded HLA-A24-Binding Synthetic Peptide Induces Specific Anti-Tumor Cytotoxic T Lymphocytes", International Journal of Cancer, vol. 80, No. 2, Jan. 18, 1999, pp. 169-172.
Gambacorti-Passerini et al., "Mapping of HLA Class I Binding Motifs in Forty-Four Fusion Proteins Involved in Human Cancers", Clinical Cancer Research, vol. 3, No. 5, May 1997, pp. 675-683.
Gao et al., "Tumor Vaccination That Enhances Antitumor T-cell Responses Does Not Inhibit the Growth of Established Tumors Even in Combination With Interleukin-12 Treatment: The Importance of Inducing Intratumoral T-cell Migration", Journal of Immunotherapy, vol. 23, No. 6, Nov. 1, 2000, pp. 643-653.
Guo et al., "Different Length Peptides Bind to HLA-Aw68 Similarly at Their Ends but Bulge Out in the Middle", Nature, vol. 360, No. 6402, Nov. 1992, pp. 364-366.
Gura , "Systems for Identifying New Drugs are Often Faulty", Science, Cancer Models, vol. 278, No. 5340, Nov. 7, 1997, pp. 1041-1042.
Harao et al., "CDCA1, A Novel Cancer-Testis Antigen Useful for Immunotherapy of Lung Cancer", Nihon Gangakkaisokai, vol. 66, 2007, 3 pages.

(56) References Cited

OTHER PUBLICATIONS

Harao et al., "Cell Division Cycle Associated 1, an Ideal Lung Cancer Antigen for Immunotherapy, Identified Using cDNA Microarray Analysis", Doctor's Thesis, 2008, pp. 1-49.

Harao et al., "Development of Cancer Immunotherapy Targeting a Novel Cancer-Testis Antigen, CDCA1, That Highly Expresses in Lung Cancer", Kibangakutekimennekikenkyuukai sokai; 2008, 4 Pages.

Harao et al., "HLA-A2-restricted CTL Epitopes of a Novel Lung Cancer-Associated Cancer Testis Antigen, Cell Division Cycle Associated 1, Can Induce Tumor-Reactive CTL", International Journal of Cancer, vol. 123, No. 11, Dec. 2008, pp. 2616-2625.

Harao et al., "Identification of a Novel Cancer-Testis Antigen, CDCA1, That is Useful for Immunotherapy for Lung Cancer", Nihon Gekagakkai, 2008, 3 pages.

Harris, "Structure and Function of the p53 Tumor Suppressor Gene: Clues for Rational Cancer Therapeutic Strategies", Journal of the National Cancer Institute, vol. 88, No. 20, Oct. 16, 1996, pp. 1442-1455.

Hayama et al., "Activation of CDCA1-KNTC2, Members of Centromere Protein Complex, Involved in Pulmonary Carcinogenesis", Cancer Research, vol. 61, No. 22, Nov. 1, 2006, pp. 10339-10348.

Hoffmann et al., "The Ability of Variant Peptides to Reverse the Nonresponsiveness of T Lymphocytes to the Wild-type Sequence P53264-272 Epitope", Journal of Immunology, vol. 168, No. 3, Feb. 1, 2002, pp. 1338-1347.

Hoof et al., "NetMHCpan, a Method for MHC Class I Binding Prediction Beyond Humans", Immunogenetics, vol. 61, No. 1, Jan. 2009, pp. 1-13.

Ishizaki et al., "Inhibition of Tumor Growth With Antiangiogenic Cancer Vaccine Using Epitope Peptides Derived From Human Vascular Endothelial Growth Factor Receptor 1", Clinical Cancer Research, vol. 12, No. 9, Oct. 1, 2006, pp. 5841-5849.

Jain, "Barriers to Drug Delivery in Solid Tumors", Scientific American, vol. 271, No. 1, Jul. 1994, pp. 58-65.

Johnson, "The Clinical Impact of Screening and Other Experimental Tumor Studies", Cancer Treatment Reviews, vol. 2, No. 1, Mar. 1975, pp. 1-31.

Juengst, "What Next for Human Gene Therapy?", British Medical Journal, vol. 326, Jun. 28, 2003, pp. 1410-1411.

Karin et al., "Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production", Journal of Experimental Medicine., vol. 180, No. 6, Dec. 1, 1994, pp. 2227-2237.

Kast et al., "Role of HLA-A Motifs in Identification of Potential CTL Epitopes in Human Papillomavirus Type 16 E6 and E7 Proteins", Journal of Immunology, vol. 152, No. 8, Apr. 15, 1994, pp. 3904-3912.

Kikuchi et al., "Identification of a SART-1-Derived Peptide Capable of Inducing HLA-A24-Restricted and Tumor-Specific Cytotoxic T Lymphocytes", International Journal of Cancer, vol. 81, No. 3, May 5, 1999, pp. 459-466.

Klebanoff et al., "Therapeutic Cancer Vaccines: Are We There Yet?", Immunological Reviews, vol. 239, No. 1, Jan. 2011, pp. 27-44.

Kondo et al., "Prominent Roles of Secondary Anchor Residues in Peptide Binding to HLA-A24 Human Class 1 Molecules", Journal of Immunology, vol. 155, No. 9, Nov. 1, 1995, pp. 4307-4312.

Kubo et al., "Definition of Specific Peptide Motifs for Four Major HLA-A Alleles", Journal of Immunology, vol. 152, No. 8, Apr. 15, 1994, pp. 3913-3924.

Liu et al., "Human NUF2 Interacts With Centromere-Associated Protein E and is Essential for a Stable Spindle Microtubule-kinetochore Attachment", The Journal of Biological Chemistry, vol. 282, No. 29, Jul. 20, 2007, pp. 21415-21424.

Marchand et al., "Biological and Clinical Developments in Melanoma Vaccines", Expert Opinion on Biological Therapy, vol. 1, No. 3, May 2001, pp. 497-510.

Marchand et al., "Tumor Regressions Observed in Patients With Metastatic Melanoma Treated With an Antigenic Peptide Encoded By Gene MAGE-3 And Presented by HLA-A1", International Journal of Cancer, vol. 80, No. 2, Jan. 18, 1999, pp. 219-230.

Marshall, "Gene Therapy's Growing Pains", Science, vol. 269, No. 5227, Aug. 25, 1995, pp. 1050-1055.

Morel et al., "Processing of Some Antigens by the Standard Proteasome but Not by the Immunoproteasome Results in Poor Presentation by Dendritic Cells", Immunity, vol. 12, No. 1, Jan. 2000, pp. 107-117.

Nabetani et al., "A Conserved Protein, Nuf2, is Implicated in Connecting the Centromere to the Spindle During Chromosome Segregation: A Link Between the Kinetochore Function and the Spindle Checkpoint", Chromosoma, vol. 110, No. 5, Sep. 2001, pp. 322-334.

Nielsen et al., "Improved Prediction of MHC Class I and Class II Epitopes Using a Novel Gibbs Sampling Approach", Bioinformatics, vol. 20, No. 9, Jun. 12, 2004, pp. 1388-1397.

Nielsen et al., "Reliable Prediction of T-Cell Epitopes Using Neural Networks With Novel Sequence Representations", Protein Science, vol. 12, No. 5, May 2003, pp. 1007-1017.

Obara et al., "Phase I Clinical Trial of Cell Division Associated 1 (CDCA1) Peptide Vaccination For Castration Resistant Prostate Cancer", Cancer Science, vol. 108, No. 7, Jul. 2017, pp. 1452-1457.

Ochoa-Garay et al., "The Ability of Peptides to Induce Cytotoxic T Cells in Vitro does not Strongly Correlate with their Affinity for the H-2Ld Molecule: Implications for Vaccine Design and Immunotherapy", Molecular Immunology, vol. 34, No. 3, Feb. 1997, pp. 273-281.

Oiso et al., "A Newly Identified MAGE-3-Derived Epitope Recognized by HLA-A24-Restricted Cytotoxic T Lymphocytes", International Journal of Cancer, vol. 81, No. 3, May 5, 1999, pp. 387-394.

Parker et al., "Scheme for Ranking Potential HLA-A2 Binding Peptides Based on Independent Binding of Individual Peptide Side-Chains", Journal of Immunology, vol. 152, No. 1, Jan. 1, 1994, pp. 163-175.

Application No. PCT/JP2019/030117, International Search Report and Written Opinion, Mailed On Oct. 15, 2019, 22 pages.

Pearson, "An Introduction to Sequence Similarity ("Homology") Searching", Current Protocols in Bioinformatics, vol. 42, No. 1, Jun. 2013, pp. 1-9.

Rammensee et al., "MHC Ligands and Peptide Motifs: First Listing", Immunogenetics, vol. 41, No. 4, Feb. 1995, pp. 178-228.

Rosenberg et al., "Cancer Immunotherapy: Moving Beyond Current Vaccines", Nature Medicine, vol. 10, No. 9, Sep. 2004, pp. 909-915.

Ross et al., "Gene Therapy in the United States: A Five-Year Status Report", Human Gene Therapy, vol. 7, No. 14, Sep. 10, 1996, pp. 1781-1790.

Rubanyi, "The Future of Human Gene Therapy", Molecular Aspects of Medicine, vol. 22, No. 3, Jun. 2001, pp. 113-142.

Schreiber et al., "Tumor Immunogenicity and Responsiveness to Cancer Vaccine Therapy; The State of the Art", Seminars in Immunology, vol. 22, No. 3, Jun. 2010, pp. 105-112.

Schueler-Furman et al., "Structure-Based Prediction of Binding Peptides to MHC Class I Molecules: Application to a Broad Range of MHC Alleles", Cambridge University Press, Protein Science, vol. 9, No. 9, Sep. 2000, pp. 1838-1846.

Sette et al., "Nine Major HLA Class I Supertypes Account for the Vast Preponderance of HLA-A and -B Polymorphism", Immunogenetics, vol. 50, Nos. 3-4, Nov. 1999, pp. 201-212.

Shastri et al., "Presentation of Endogenous Peptide/MHC Class I Complexes is Profoundly Influenced by Specific C-Terminal Flanking Residues.", The Journal of Immunology, vol. 155, No. 9, Nov. 1, 1995, pp. 4339-4346.

Sidney et al., "Definition of an HLA-A3-Like Supermotif Demonstrates the Overlapping Peptide-Binding Repertoires of Common HLA Molecules", Human Immunology, vol. 45, No. 2, Feb. 1996, pp. 79-93.

Sidney et al., "HLA Class 1 Supertypes: A Revised and Updated Classification", BMC Immunology, vol. 9, No. 1, Jan. 22, 2008, 15 pages.

Spitler, "Cancer Vaccines: The Interferon Analogy", Cancer Biotherapy, vol. 10, No. 1, 1995, pp. 1-3.

(56) References Cited

OTHER PUBLICATIONS

Stills, "Adjuvants and Antibody Production: Dispelling the Myths Associated with Freund's Complete and Other Adjuvants", ILAR journal, vol. 46, No. 3, 2005, pp. 280-293.
Takiguchi et al., "Analysis of Three HLA-A*3303 Binding Peptide Anchors Using an HLA-A*3303 Stabilization Assay", Tissue Antigens, vol. 55, No. 4, Apr. 2000, pp. 296-302.
Tanaka et al., "Induction of Antitumor Cytotoxic T Lymphocytes With a MAGE-3-Encoded Synthetic Peptide Presented by Human Leukocytes Antigen-A24", Cancer Research, vol. 57, No. 20, Oct. 15, 1997, pp. 4465-4468.
Tokuriki et al., "Stability Effects of Mutations and Protein Evolvability", Current Opinion in Structural Biology, vol. 19, No. 5, Oct. 2009, pp. 596-604.
Van Der Burg et al., "Immunogenicity of Peptides Bound to MHC Class I Molecules Depends on the MHC-Peptide Complex Stability", Journal of Immunology, vol. 156, No. 9, May 1, 1996, pp. 3308-3314.
Verma et al., "Gene Therapy—Promises, Problems and Prospects", Nature, vol. 389, No. 6648, Sep. 18, 1997, pp. 239-242.
Vissers et al., "The Renal Cell Carcinoma-associated Antigen G250 Encodes a Human Leukocyte Antigen (HLA)-A2.1-restricted Epitope Recognized by Cytotoxic T Lymphocyte", Cancer Research, American Association for Cancer Research, vol. 59, No. 21, Nov. 1, 1999, pp. 5554-5559.
Walker, "Drug Target Discovery by Gene Expression Analysis: Cell Cycle Genes", Current Cancer Drug Targets, vol. 1, No. 1, May 2001, pp. 73-83.
Wells, "Additivity of Mutational Effects in Protein", Biochemistry, vol. 29, No. 37, Sep. 18, 1990, pp. 8509-8517.
Wigge et al., "The Ndc80p Complex From *Saccharomyces cerevisiae* Contains Conserved Centromere Components and Has a Function in Chromosome Segregation", Journal of Cell Biology, vol. 152, No. 2, Jan. 22, 2001, pp. 349-360.
Zaremba et al., "Identification of an Enhancer Agonist Cytotoxic T Lymphocyte Peptide From Human Carcinoembryonic Antigen", Cancer Research, vol. 57, No. 20, Oct. 15, 1997, pp. 4570-4577.
Zips et al., "New Anticancer Agents: In Vitro and In Vivo Evaluation", In Vivo, vol. 19, No. 1, Jan. 2005, pp. 1-7.
Harao, "Cell Division Cycle Associated 1, an Ideal Lung Cancer Antigen for Immunotherapy, Identified Using cDNA Microarray Analysis", Doctor's Thesis, 2008, pp. 1-49.
Hayama et al., "Activation of CDCA1-KNTC2, Members of Centromere Protein Complex, Involved in Pulmonary Carcinogenesis", Cancer Res. Nov. 1, 2006;66(21):10339-48.
Ishizaki et al., "Inhibition of Tumor Growth With Antiangiogenic Cancer Vaccine Using Epitope Peptides Derived From Human Vascular Endothelial Growth Factor Receptor 1", Clin Cancer Res. Oct. 1, 2006;12(19):5841-9.
Johnson et al., "The Clinical Impact of Screening and Other Experimental Tumor Studies", Cancer Treatment Reviews, vol. 2, No. 1, Mar. 1975, pp. 1-31.
Filippovich et al., "Biochemical Bases of Human Life", Textbook for Higher Educational Institutions; Moscow, Vlados, 2005, 407; 49-50, 70.
Lee et al., "Increased Vaccine-Specific T Cell Frequency After Peptide-Based Vaccination Correlates with Increased Susceptibility to In Vitro Stimulation But Does Not Lead to Tumor Regression", J. Immunol., Dec. 1, 1999; 163(11):6292-6300.
Pakula et al., "Genetic Analysis of Protein Stability and Function", Annu. Rev. Genet., 1989; 23:289-310.
Seliverstov et al., "Spinal Muscular Atrophies: Concept, Differential Diagnosis, Treatment Prospects", Nervnye bolezni, 2015; 3:9-17.

\* cited by examiner

CDCA1-DERIVED PEPTIDE AND VACCINE CONTAINING SAME

CROSS-REFERENCE TO RELATED APPLICATIONS

The present application is a continuation of U.S. application Ser. No. 17/264,277, filed Jan. 28, 2021, which is a § 371 National Phase Application of PCT/JP2019/030117, filed Aug. 1, 2019, which application claims the benefit of Japanese Patent Application No. JP 2018-145607, filed Aug. 2, 2018, the entire contents of which are incorporated by reference in their entireties for all purposes herein.

TECHNICAL FIELD

The present invention relates to the field of biological science, more specifically to the field of cancer therapy. In particular, the present invention relates to novel peptides that are effective as cancer vaccines, methods for either or both of treating and preventing cancers using the peptide(s), and pharmaceutical compositions comprising the peptide(s).

BACKGROUND ART

Cytotoxic T lymphocytes (CTLs) have been known to recognize epitope peptides derived from the tumor-associated antigens (TAAs) presented on the major histocompatibility complex (MHC) class I molecule, which is expressed on tumor cell surface, and then kill the tumor cells. To date, many TAAs including the melanoma antigen (MAGE) family have been discovered through immunological approaches (NPL1: Boon T, Int J Cancer 1993, 54(2):177-80; NPL2: Boon T & van der Bruggen P, J Exp Med 1996, 183(3):725-9). Immunotherapies targeting these TAAs are currently undergoing clinical development.

In some TAAs, epitope peptides that can be recognized by CTLs were identified and their application on immunotherapy for various cancers is anticipated (NPL3: Harris C C, J Natl Cancer Inst 1996, 88(20): 1442-55; NPL4: Butterfield L H et al., Cancer Res 1999, 59(13): 3134-42; NPL5: Vissers J L et al., Cancer Res 1999, 59(21): 5554-9; NPL6: van der Burg S H et al., J Immunol 1996, 156(9): 3308-14; NPL7: Tanaka F et al., Cancer Res 1997, 57(20): 4465-8; NPL8: Fujie T et al., Int J Cancer 1999, 80(2): 169-72; NPL9: Kikuchi M et al., Int J Cancer 1999, 81(3): 459-66; NPL10: Oiso M et al., Int J Cancer 1999, 81(3): 387-94). Until now, several clinical trials for cancer immunotherapy using these TAA-derived CTL epitope peptides have been reported. Unfortunately, however, in many of these clinical trials, the response rate is not necessarily high (NPL11: Belli F et al., J Clin Oncol 2002, 20(20): 4169-80; NPL12: Coulie P G et al., Immunol Rev 2002, 188: 33-42; NPL13: Rosenberg S A et al., Nat Med 2004, 10(9): 909-15). Therefore, there is still demand for identification of novel epitope peptides that are applicable to cancer immunotherapy.

CDCA1 (cell division cycle associated 1; also described as NUF2, NDC80 kinetochore complex component: Nuf2; reference sequence: GeneBank Accession Number NM_145697 (SEQ ID NO: 44) or GeneBank Accession Number NM_031423 (SEQ ID NO: 46)) has been identified as a member of the genes co-expressed with CDC2, cyclin, topoisomerase II and other cell cycle genes (NPL14: Walker et al., Curr Cancer Drug Targets 2001, 1(1): 73-83). CDCA1 has been found to be related to the centromere of HeLa cells undergoing mitotic division, and is considered to be a functional homologue of yeast Nuf2 (NPL15: Wigge P A et al., J Cell Biol 2001, 152(2): 349-60). Meanwhile, CDCA1 has been identified as a gene showing elevated expression in non-small cell lung cancer by gene expression profiling based on a genome-wide cDNA microarray targeting 27648 genes (NPL16: Hayama et al., Cancer Res 2006, 66(21): 10339-48; PTL1: WO2007/013480; PTL2: WO2005/089735). The CDCA1 expression is observed in lung cancer tissues and lung cancer cell lines, but little expression is observed in 22 normal tissues except the testis (NPL16; PTL1). Further, as a result of siRNA-mediated suppression of the CDCA1 expression, suppression of cell proliferation in CDCA1-expressing lung cancer cell lines is caused (NPL16; PTLs 1-2). Moreover, elevated expression of CDCA1 is also observed in various cancers such as cholangiocellular cancer, bladder cancer and renal cell cancer (NPL17: Harao M et al., Int J Cancer 2008, 123(11): 2616-25).

Recently, CDCA1-derived HLA-A02-restricted CTL epitope peptides (NPL17: Harao et al., Int J Cancer. 2008, 123(11): 2616-25; PTL3: WO2009/025117), HLA-A24-restricted CTL epitope peptides (PTL4: WO2009/153992), HLA-A11-restricted CTL epitope peptides (PTL5: WO2016/021508), HLA-A33-restricted CTL epitope peptides (PTL5: WO2016/021508) and HLA-A03-restricted CTL epitope peptides (PTL5: WO2016/021508) have been identified. Therapeutic effects by these peptides are expected in cancer patients having the HLA-A02 type, HLA-A24 type, HLA-A11 type, HLA-A33 type or HLA-A03 type, but for cancer patients having HLA types other than those, peptides corresponding to respective HLA type are desired.

CITATION LIST

Patent Literature

[PTL 1] WO2007/013480
[PTL 2] WO2005/089735
[PTL 3] WO2009/025117
[PTL 4] WO2009/153992
[PTL 5] WO2016/021508

Non Patent Literature

[NPL 1] Boon T, Int J Cancer 1993, 54(2): 177-80
[NPL 2] Boon T & van der Bruggen P, J Exp Med 1996, 183(3): 725-9
[NPL 3] Harris C C, J Natl Cancer Inst 1996, 88(20): 1442-55
[NPL 4] Butterfield L H et al., Cancer Res 1999, 59(13): 3134-42
[NPL 5] Vissers J L et al., Cancer Res 1999, 59(21): 5554-9
[NPL 6] van der Burg S H et al., J Immunol 1996, 156(9): 3308-14
[NPL 7] Tanaka F et al., Cancer Res 1997, 57(20): 4465-8
[NPL 8] Fujie T et al., Int J Cancer 1999, 80(2): 169-72
[NPL 9] Kikuchi M et al., Int J Cancer 1999, 81(3): 459-66
[NPL 10] Oiso M et al., Int J Cancer 1999, 81(3): 387-94
[NPL 11] Belli F et al., J Clin Oncol 2002, 20(20): 4169-80
[NPL 12] Coulie P G et al., Immunol Rev 2002, 188: 33-42
[NPL 13] Rosenberg S A et al., Nat Med 2004, 10(9): 909-15
[NPL 14] Walker et al., Curr Cancer Drug Targets 2001, 1(1): 73-83
[NPL 15] Wigge P A et al., J Cell Biol 2001, 152(2): 349-60
[NPL 16] Hayama et al., Cancer Res 2006, 66(21): 10339-48
[NPL 17] Harao et al., Int J Cancer 2008, 123(11): 2616-25

SUMMARY OF THE INVENTION

The present invention relates to peptides that can induce cytotoxic T cells (CTLs) specifically responding to CDCA1- expressing cells. When these peptides are presented on antigen-presenting cells (APCs) by the human leukocyte antigen (HLA) and recognized by CD8-positive T cells, CTLs that show a peptide-specific cytotoxic activities are induced. CDCA1-derived peptides that have been identified so far to have CTL-inducing ability (CTL inducibility) are HLA-A02-restricted, HLA-A24-restricted, HLA-A11-restricted, HLA-A33-restricted, or HLA-A03-restricted peptides, and when antigen-presenting cells do not express these HLAs, the peptides cannot induce CTLs. Therefore, conventional peptides are not suitable for performing immunotherapy on cancer patients (subjects) that do not have these HLAs. HLA-A01 is an HLA allele highly frequently observed in Caucasians (Cao K et al., Hum Immunol 2001, 62(9): 1009-30). It is desirable to administer HLA-A01-restricted peptides to HLA-A01-positive cancer patients. Hence, the present invention relates to CDCA1-derived peptides with CTL-inducing ability that are restrictive to HLA-A01. Based on results disclosed herein, the peptides of the present invention have been proven to be epitope peptides that can induce a potent and specific immune response against cancer cells expressing CDCA1 and HLA-A01.

Therefore, one of the objectives of the present invention is to provide CDCA1-derived peptides that can induce CTLs in an HLA-A01-restrictive manner. These peptides can be used to induce CTLs in vitro, ex vivo or in vivo, or can be used to administer to subjects for the purpose of inducing an immune response against CDCA1-expressing cancer cells. Preferable peptides are peptides comprising the amino acid sequence selected from among SEQ ID NOs: 1, 8, 10, 13, 25, 33 to 35 and 37; more preferable peptides are nonapeptides or decapeptides; and even more preferable peptides are peptides consisting of the amino acid sequence selected from among SEQ ID NOs: 1, 8, 10, 13, 25, 33 to 35 and 37.

The peptides of the present invention encompass peptides in which one, two, or more amino acid(s) is/are substituted, deleted, inserted and/or added, as long as the resultant modified peptides retain the CTL-inducing ability of the original peptide.

The present invention further provides isolated polynucleotides encoding any one of the peptides of the present invention. Similar to the peptides of the present invention, these polynucleotides can be used for inducing APCs with CTL-inducing ability, and can be administered to subjects for inducing an immune response against CDCA1-expressing cancer cells.

The present invention also provides compositions comprising one or more types of peptides of the present invention, one or more types of polynucleotides encoding one or more types of peptides of the present invention, APCs of the present invention, exosomes presenting peptides of the present invention, and/or CTLs of the present invention. The compositions of the present invention are preferably pharmaceutical compositions. The pharmaceutical compositions of the present invention can be used for treating and/or preventing cancer, as well as preventing postoperative recurrence thereof. They can also be used for inducing an immune response against cancer. When administered to a subject, a peptide of the present invention is presented on the surface of an APC, and as a result CTLs targeting the peptide are induced. Therefore, another objective of the present invention is to provide compositions for inducing CTLs, wherein the compositions comprise one or more types of peptides of the present invention, one or more types of polynucleotides encoding one or more types of peptides of the present invention, APCs of the present invention, and/or exosomes presenting peptides of the present invention.

A further objective of the present invention is to provide methods of inducing APCs having CTL-inducing ability, wherein the methods comprise a step of contacting one or more types of peptides of the present invention with an APC, or a step of introducing a polynucleotide encoding any one peptide of the present invention into an APC.

The present invention further provides a method of inducing CTLs, comprising a step of co-culturing a CD8-positive T cell with an APC that presents on its surface a complex of an HLA antigen and a peptide of the present invention, a step of co-culturing a CD8-positive T cell with an exosome that presents on its surface a complex of an HLA antigen and a peptide of the present invention, or a step of introducing into a CD8-positive T cell a vector comprising a polynucleotide encoding each subunit of a T cell receptor (TCR) capable of binding to a peptide of the present invention presented by an HLA antigen on a cell surface.

A further objective of the present invention is to provide isolated APCs that present on their surface a complex of an HLA antigen and a peptide of the present invention. The present invention further provides isolated CTLs targeting a peptide of the present invention. These APCs and CTLs can be used in immunotherapy for CDCA1-expressing cancers.

Another objective of the present invention is to provide methods of inducing an immune response against cancer in a subject, wherein the methods comprise a step of administering to the subject a composition(s) comprising a peptide(s) of the present invention or a polynucleotide(s) encoding the peptide(s), an APC(s) of the present invention, an exosome(s) presenting a peptide(s) of the present invention, and/or a CTL(s) of the present invention. Another objective of the present invention is to provide methods of treating and/or preventing cancer, as well as preventing postoperative recurrence thereof in a subject, wherein the methods comprise a step of administering to the subject a peptide(s) of the present invention, a polynucleotide(s) encoding the peptide(s), an APC(s) of the present invention, an exosome(s) presenting a peptide(s) of the present invention, and/or a CTL(s) of the present invention.

In addition to the above, other objects and features of the present invention will become more fully apparent when the following detailed description is read in conjunction with the accompanying figures and examples. However, it is to be understood that both the foregoing summary of the present invention and the following detailed description are of exemplified embodiments, and not restrictive of the present invention or other alternate embodiments of the present invention. In particular, while the present invention is described herein with reference to a number of specific embodiments, it will be appreciated that the description is illustrative of the present invention and is not constructed as limiting of the present invention. Various modifications and applications may occur to those who are skilled in the art, without departing from the spirit and the scope of the present invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

assay performed using cells induced using peptides derived from CDCA1. In the figure, "+" shows IFN-gamma production against target cells pulsed with a peptide of interest and "−" shows IFN-gamma production against target cells that have not been pulsed with any peptides (negative control). In comparison with the negative control, peptide-specific IFN-gamma production was observed in:

Well #1 with CDCA1-A01-8-138 (SEQ ID NO: 1) (a),
Well #7 with CDCA1-A01-9-290 (SEQ ID NO: 25) (b),
Well #5 with CDCA1-A01-9-130 (SEQ ID NO: 33) (c),
Well #7 with CDCA1-A01-9-246 (SEQ ID NO: 34) (d),
Well #1 with CDCA1-A01-9-268 (SEQ ID NO: 35) (e),
Well #3 with CDCA1-A01-9-288 (SEQ ID NO: 37) (f),
Well #2 with CDCA1-A01-10-136 (SEQ ID NO: 8) (g),
Well #6 with CDCA1-A01-10-56 (SEQ ID NO: 10) (h), and
Well #6 with CDCA1-A01-10-48 (SEQ ID NO: 13) (i)

CTL clones were established from the boxed cells in the photos that showed a reaction. In contrast, CDCA1-A01-10-66 (SEQ ID NO: 9) (j) is shown as an example of typical negative data where peptide-specific IFN-gamma production was not observed.

Figure 2:
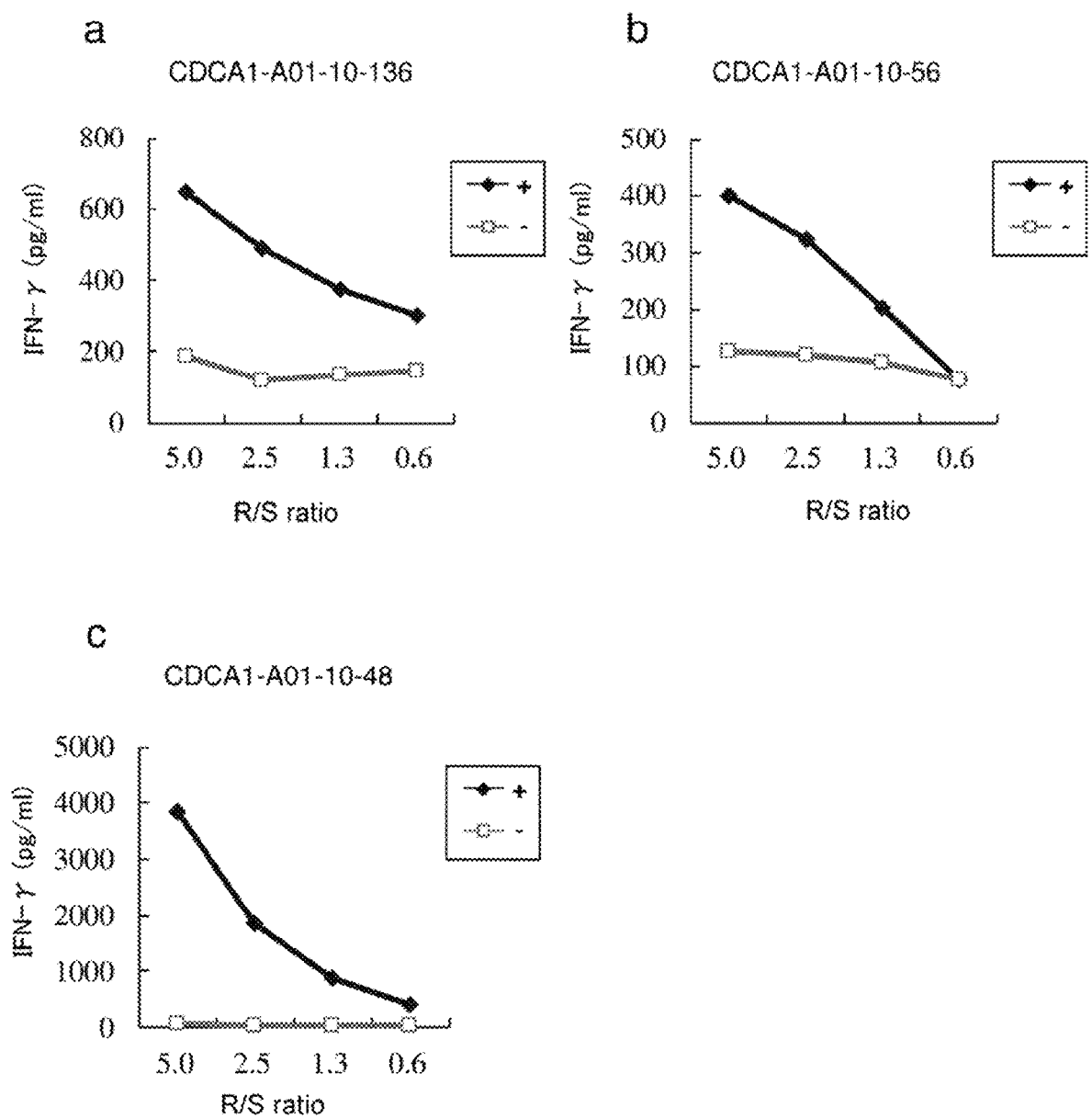

FIG. 2 is comprised of a series of line graphs (a) to (c) showing IFN-gamma production of CTL clones established by limiting dilution method following induction by CDCA1-A01-10-136 (SEQ ID NO: 8), CDCA1-A01-10-56 (SEQ ID NO: 10), or CDCA1-A01-10-48 (SEQ ID NO: 13). These results show peptide-specific IFN-gamma production of the CTL clones. In the figure, "+" shows IFN-gamma production of the CTL clones against target cells pulsed with a peptide of interest and "−" shows IFN-gamma production of the CTL clones against target cells that have not been pulsed with any peptides. The R/S ratio indicates the ratio of the cell number of the CTL clones (Responder cells) and the cell number of target cells that stimulate these cells (Stimulator cells).

Figure 3:
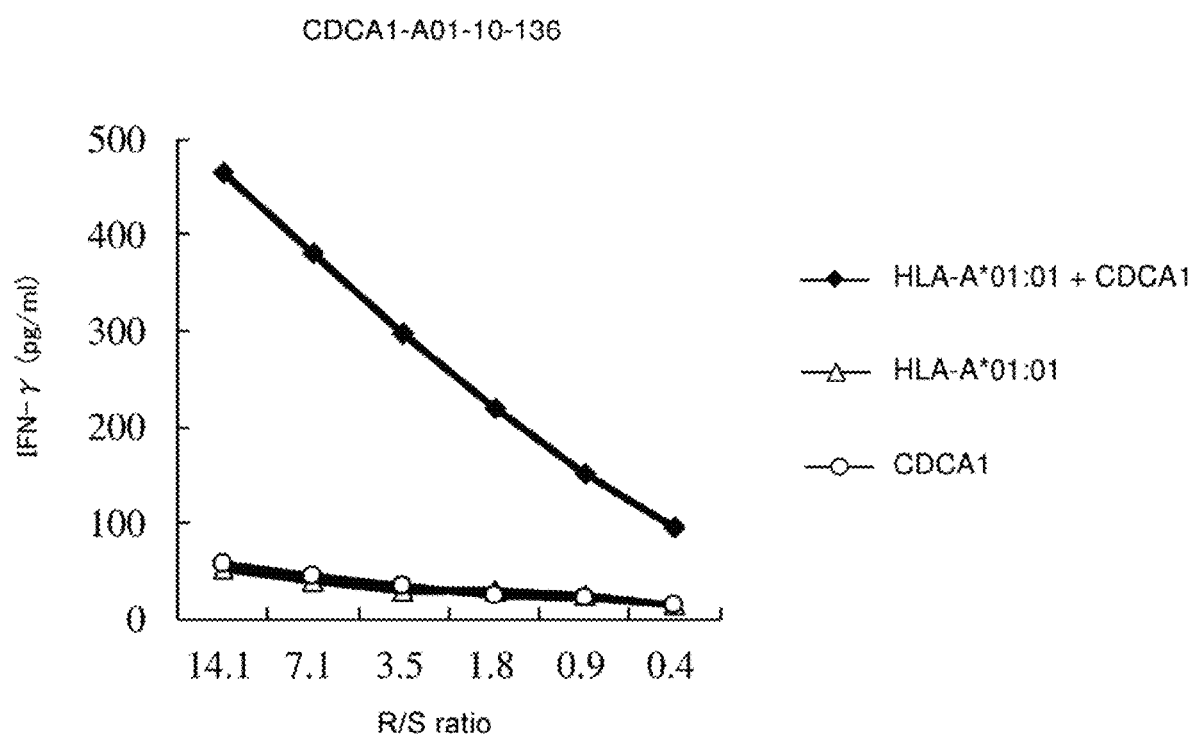

FIG. 3 is a line graph showing IFN-gamma production of a CTL clone against target cells expressing both CDCA1 and HLA-A*01:01. COS7 cells expressing either HLA-A*01:01 or the full-length CDCA1 gene served as a negative control. The CTL clone established following induction by CDCA1-A01-10-136 (SEQ ID NO: 8) showed IFN-gamma production in COS7 cells into which both CDCA1 and HLA-A*01:01 genes were introduced (black diamond). Meanwhile, it did not show significant IFN-gamma production in COS7 cells into which either HLA-A*01:01 (triangle) or CDCA1 (white circle) was introduced.

MODE FOR CARRYING OUT THE INVENTION

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

I. Definitions

The words "a", "an", and "the" as used herein mean "at least one" unless otherwise specifically indicated.

The terms "isolated" and "purified" used in relation with a substance (for example, peptide, antibody, polynucleotide or such) indicate that the substance does not substantially contain at least one substance that may else be included in a natural source. Thus, an isolated or purified peptide refers to a peptide that does not substantially contain another cellular material, for example, carbohydrate, lipid and other contaminating proteins from the cell or tissue source from which the peptide is derived. When the peptide is chemically synthesized, an isolated or purified peptide refers to a peptide that does not substantially contain a precursor substance or another chemical substance. The phrase "does not substantially contain a cellular material" includes peptide preparations in which the peptide is separated from cellular components of the cells from which it is isolated or recombinantly produced. Thus, a peptide that does not substantially contain a cellular material encompasses peptide preparations that contain less than about 30%, 20%, 10%, or 5%, 3%, 2% or 1% (dry weight basis) of other cellular materials. When the peptide is recombinantly produced, an isolated or purified peptide does not substantially contain culture medium, which encompasses peptide preparations that contain culture medium less than about 20%, 10%, or 5%, 3%, 2% or 1% (dry weight basis) of the volume of the peptide preparation. When the peptide is generated by chemical synthesis, an isolated or purified peptide does not substantially contain a precursor substance or other chemical substances, which encompasses peptide preparations that contain a precursor substance or other chemical substances less than about 30%, 20%, 10%, 5%, 3%, 2% or 1% (dry weight basis) of the volume of the peptide preparation. That a particular peptide preparation is an isolated or purified peptide can be confirmed, for example, by the appearance of a single band following sodium dodecyl sulfate (SDS)-polyacrylamide gel electrophoresis and Coomassie Brilliant Blue staining or such of the gel. In a preferred embodiment, the peptides and polynucleotides of the present invention are isolated or purified.

The terms "polypeptide", "peptide" and "protein" are used interchangeably herein, and refer to polymers of amino acid residues. These terms are applied to also non-naturally occurring amino acid polymers comprising one or more non-naturally occurring amino acid residues, in addition to naturally occurring amino acid polymers. Non-naturally occurring amino acids include amino acid analogs, amino acid mimetics, and such.

The term "amino acid" as used herein refers to naturally occurring amino acids, as well as amino acid analogs and amino acid mimetics that functions similarly to the naturally occurring amino acids. Naturally occurring amino acids are those encoded by the genetic code, as well as those modified after translation in cells (e.g., hydroxyproline, gamma-carboxyglutamate, and O-phosphoserine, etc.). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine sulfoxide, methionine methyl sulfonium, and such). The phrase "amino acid mimetic" refers to chemical compounds that have different structures but similar functions to general amino acids. Amino acids can be either L-amino acids or D-amino acids, and the peptides of the present invention are preferably L-amino acid polymers.

The terms "polynucleotide", "oligonucleotide" and "nucleic acid" are used interchangeably herein, and refer to a polymer of nucleotides.

The term "composition" used in the present specification is intended to encompass products that include specified ingredients in specified amounts, and any products generated directly or indirectly from combination of specified ingredients in the specified amounts. When the composition is a pharmaceutical composition, the term "composition" is intended to encompass products including active ingredient(s) and inert ingredient(s), as well as any products generated directly or indirectly from combination, complexation or aggregation of any two or more ingredients, from dissociation of one or more ingredients, or from other types of reactions or interactions of one or more ingredients. Thus, the pharmaceutical compositions of the present invention encompass any compositions made by admixing compounds or cells of the present invention with a pharmaceutically or physiologically acceptable carrier. Without being limited thereto, the terms "pharmaceutically acceptable carrier" or "physiologically acceptable carrier" used in the present specification include liquid or solid bulking agents, diluents, excipients, solvents, and encapsulation materials; and mean pharmaceutically or physiologically acceptable materials, compositions, substances or media.

Unless otherwise specified, the term "cancer" refers to a cancer that overexpresses the CDCA1 gene; and examples thereof include bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue tumor, colon cancer and such, without being limited thereto. In an exemplary embodiment, the "cancer" is a cancer that expresses CDCA1 and HLA-A01.

Unless otherwise specified, the terms "cytotoxic T lymphocyte" and "cytotoxic T cell" and "CTL" are used interchangeably herein. Unless otherwise specifically indicated, they refer to a sub-group of T lymphocytes that can recognize non-self cells (for example, tumor/cancer cells, virus-infected cells) and induce the death of such cells.

Unless otherwise specified, the term "HLA-A01 (HLA-A1)" refers to the HLA-A01 type which includes subtypes such as HLA-A*01:01, HLA-A*01:02, HLA-A*01:03, and HLA-A*01:04.

In the context of a subject or patient, the phrase "HLA antigen of a subject (or patient) is HLA-A01" used herein refers to that a subject or patient has the HLA-A01 antigen gene homozygously or heterozygously as the MHC (Major Histocompatibility Complex) Class I molecule, and that the HLA-A01 antigen is expressed in the cells of the subject or patient as the HLA antigen.

As long as the methods and compositions of the present invention are useful in the context of cancer "treatment", the treatment is considered "efficacious" when it achieves clinical advantages, for example, reduction in the size, spreading or metastatic ability of cancer, retardation of cancer progression, alleviation of clinical symptoms of cancer, prolongation of survival period, suppression of postoperative recurrence in a subject. When the treatment is applied prophylactically, "efficacious" means that the treatment retards or prevents cancer formation, or prevents or alleviates clinical symptoms of cancer. Effectiveness is determined in relation to any publicly known method for diagnosing or treating a specific tumor type.

As long as the methods and compositions of the present invention are useful in the context of cancer "prevention (prophylaxis)", the term "prevention (prophylaxis)" herein includes any work that eases the load of disease-associated mortality or morbidity. Prevention (Prophylaxis) can be carried out at the "primary, secondary and tertiary prevention (prophylaxis) levels". Whereas the primary prevention (prophylaxis) avoids the development of a disease, prevention (prophylaxis) at the secondary and tertiary levels encompasses prevention (prophylaxis) of disease progression and appearance of symptoms, as well as workings intended to reduce adverse effects of the existing disease by restoring functions and reducing disease-associated complications. Alternately, prevention (prophylaxis) can include alleviation of severity of a specific disorder, for example, extensive preventive therapy intended to reduce tumor growth and metastasis.

In the context of the present invention, the treatment and/or prevention (prophylaxis) of cancer and/or prevention (prophylaxis) of postoperative recurrence thereof include either of the events such as inhibition of cancer cell proliferation, tumor involution or regression, induction of remission and suppression of cancer development, tumor regression, as well as reduction or inhibition of metastasis, suppression of postoperative recurrence of cancer, and prolongation of survival period. Effective treatment and/or prevention (prophylaxis) of cancer reduce mortality, improve prognosis of an individual with cancer, reduce the blood levels of tumor markers, and alleviate detectable symptoms associated with cancer. For example, alleviation or improvement of symptoms constitutes effective treatment and/or prevention (prophylaxis), and includes a condition in which the symptoms are alleviated or stable by 10%, 20%, 30% or more.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an "antibody" herein is used in the broadest sense and specifically covers intact monoclonal antibodies, polyclonal antibodies, multispecific antibodies (e.g., bispecific antibodies) formed from two or more intact antibodies, and antibody fragments so long as they exhibit the desired biological activity. An "antibody" may be antibodies of all classes (e.g., IgA, IgD, IgE, IgG and IgM).

Unless otherwise specified, the technical terms and scientific terms used herein all have the same meanings as terms commonly understood by one of ordinary skill in the art to which the present invention belongs.

II. Peptides

HLA-A01 is an HLA allele commonly seen in Caucasians (Cao et al., Hum Immunol 2001, 62(9): 1009-30). Thus, an effective method of treating CDCA1-expressing cancers for a great population of Caucasians can be provided by providing CDCA1-derived CTL-inducing peptides restricted to HLA-A01. Thus, the present invention provides CDCA1-derived peptides that are capable of inducing CTLs in an HLA-A01-restrictive manner.

The peptides of the present invention are CDCA1-derived peptides that are capable of inducing CTLs in an HLA-A01-restrictive manner. Peptides capable of inducing CTLs in an HLA-A01-restrictive manner include peptides having the amino acid sequence selected from among SEQ ID NOs: 1, 8, 10, 13, 25, 33 to 35 and 37.

CTLs having a cytotoxic activity specific to these peptides can be established by in vitro stimulation of T cells by dendritic cells pulsed with these peptides. The established CTLs show a specific cytotoxic activity against target cells pulsed with each of the peptides.

The CDCA1 gene is overexpressed in cancer cells such as cancer cells in, for example, bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue tumor, colon cancer and such, but is not expressed in most normal organs. It is thus an excellent target for immunotherapy. Therefore, the peptides of the present invention can be suitably used for cancer immunotherapy. A preferred peptide is a nonapeptide (a peptide consisting of 9 amino acid residues) or a decapeptide (a peptide consisting of 10 amino acid residues), and it is more preferably a peptide consisting of the amino acid sequence selected from among SEQ ID NOs: 1, 8, 10, 13, 25, 33 to 35 and 37. For example, a peptide having the amino acid sequence of SEQ ID NO: 8 is suitable for induction of CTLs that show a specific cytotoxic activity against cells expressing HLA-A01 and CDCA1, and can be suitably used for cancer immunotherapy in HLA-A01-positive patients. In a more preferred embodiment, the peptide of the present invention is a peptide consisting of the amino acid sequence of SEQ ID NO: 8.

For the peptides of the present invention, an additional amino acid residue(s) can be made to adjoin the amino acid sequence of the peptide of the present invention, as long as the resultant peptides retain the CTL-inducing ability of the original peptide. The additional amino acid residue(s) may be composed of any types of amino acid(s), as long as they do not impair the CTL-inducing ability of the original peptide. Therefore, the peptides of the present invention encompass peptides having CTL-inducing ability, comprising the amino acid sequence selected from among SEQ ID NOs: 1, 8, 10, 13, 25, 33 to 35 and 37. Such peptides are, for example, less than about 40 amino acids, in many cases less than about 20 amino acids, and usually less than about 15 amino acids. Therefore, if the original peptide is a nonapeptide, the peptide of the present invention encompasses peptides that are 10 amino-acid long or 11-40 amino-acid long, which are produced by adjoining additional amino acid(s) to the peptide. Furthermore, if the original peptide is a decapeptide, the peptide of the present invention encompasses peptides that are 11-40 amino-acid long. Such a peptide can be, for example, a peptide that is 11-20 amino-acid long or a peptide that is 11-15 amino-acid long. A preferred example of an additional amino acid residue(s) is an amino acid residue(s) adjacent to the amino acid sequence of the peptide of the present invention in the full-length amino acid sequence of CDCA1 (for example, SEQ ID NO: 64). Therefore, the peptides of the present invention encompass peptides comprising the amino acid sequence selected from among SEQ ID NOs: 1, 8, 10, 13, 25, 33 to 35 and 37, and wherein the peptides are peptide fragments of CDCA1 and have CTL-inducing ability.

In general, modifications of one, two or more amino acids in a certain peptide do not affect the functions of the peptide, or in some cases even enhance the desired functions of the original peptide. In fact, modified peptides (i.e., peptides composed of the amino acid sequence in which one, two or several amino acid residues are modified (i.e., substituted, deleted, inserted, and/or added) compared to the original reference sequence) are known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention can be peptides comprising the amino acid sequence in which one, two or several amino acids are substituted, deleted, inserted and/or added to the amino acid sequence selected from among SEQ ID NOs: 1, 8, 10, 13, 25, 33 to 35 and 37 and having CTL-inducing ability.

On skilled in the art can recognize that individual substitutions to an amino acid sequence that alter a single amino acid or a small percentage of amino acids tend to result in the conservation of the properties of the original amino acid side chain(s). Accordingly, those are frequently referred to as "conservative substitutions" or "conservative modifications"; and modification of a protein by "conservative substitution" or "conservative modification" may result in a modified protein that has similar functions as the original protein. Tables of conservative substitutions presenting functionally similar amino acids are well known in the art. Examples of amino acid side chain characteristics that functionally resemble include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also encompassed in peptides of the present invention. However, peptides of the present invention are not restricted thereto and can include non-conservative modifications, so long as the modified peptide retains the CTL-inducing ability of the original peptide. Furthermore, modified peptides do not exclude CTL inducible peptides derived from polymorphic variants, interspecies homologues, and alleles of CDCA1.

So long as a peptide retains the CTL-inducing ability of an original peptide, one can modify (i.e., substitute, delete, insert and/or add) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, even more preferably 10% or less or 1 to 5%.

When used in the context of immunotherapy, peptides of the present invention are presented on the surface of a cell or exosome, preferably as a complex with an HLA antigen. Therefore, it is preferable that the peptides of the present invention possess high binding affinity to the HLA antigen. To that end, the peptides can be modified by substitution, deletion, insertion, and/or addition of the amino acid residues to yield a modified peptide having improved binding affinity. Since the regularity of the sequences of peptides displayed by binding to HLA antigens is already known (Falk et al., Immunogenetics 1994, 40 232-41; Chujoh, et al., Tissue Antigens 1998, 52: 501-9; Takiguchi et al., Tissue Antigens 2000, 55: 296-302.), modifications based on such regularity can be introduced into the peptides of the present invention.

For example, in peptides having binding affinity for HLA Class I, the second amino acid from the N terminus and the C-terminal amino acid are generally anchor residues involved in the binding to HLA Class I (Rammensee H G, et al., Immunogenetics. 1995, 41(4): 178-228.). For example, for HLA-A01, aspartic acid and glutamic acid for the third amino acid from the N terminus, and tyrosine for the C-terminal amino acid are known as anchor residues with high binding affinity for HLA-A01. Further, in HLA-A01, there is auxiliary anchor residues at position 2 from the N terminus; and it is known that threonine and serine are preferred as the second amino acid from the N terminus (Kubo, R. T Journal of Immunology 1994, 152: 3913-24; Gambacorti-Passerini, C. Clinical Cancer Research 1997, 3: 675-83; Falk, K. Immunogenetics 1994, 40: 238-41). Thus, to enhance the HLA-A01-binding affinity, there is a possibility that it is desirable to substitute the third amino acid from the N terminus with aspartic acid or glutamic acid, and/or to substitute the C-terminal amino acid with tyrosine. Further, there is a possibility that it is also desirable to substitute the second amino acid from the N terminus with threonine or serine. Thus, peptides with CTL-inducing ability, comprising an amino acid sequence in which, in the amino acid sequence selected from among SEQ ID NOs: 1, 8, 10, 13, 25, 33 to 35 and 37, the second amino acid from the N terminus is substituted with threonine or serine; the third amino acid from the N terminus is substituted with aspartic acid or glutamic acid; and/or the C-terminal amino acid is substituted with tyrosine are encompassed by the peptides of the present invention. In a preferred embodiment, the peptide of the present invention can be a peptide having CTL-inducing ability that consists of an amino acid sequence in which, in the amino acid sequence selected from among SEQ ID NOs: 1, 8, 10, 13, 25, 33 to 35 and 37, the second amino acid from the N terminus is substituted with threonine or serine; the third amino acid from the N terminus is substituted with aspartic acid or glutamic acid; and/or the C-terminal amino acid is substituted with tyrosine. That is, the peptides of the present invention encompass peptides having CTL-inducing ability, which comprise an amino acid sequence with one or more substitutions selected from (a) to (c) below in the amino acid sequence selected from among SEQ ID NOs: 1, 8, 10, 13, 25, 33 to 35 and 37:
  (a) the second amino acid from the N terminus is substituted with threonine or serine;
  (b) the third amino acid from the N terminus is substituted with aspartic acid or glutamic acid; and
  (c) the C-terminal amino acid is substituted with tyrosine.

In a preferred embodiment, the peptide of the present invention may be a peptide having CTL-inducing ability that consists of an amino acid sequence in which one or more substitutions selected from (a) to (c) above are introduced into the amino acid sequence selected from among SEQ ID NOs: 1, 8, 10, 13, 25, 33 to 35 and 37. In the present invention, the preferred number of substitutions is 1, 2 or 3 substitutions selected from (a) to (c) above.

Furthermore, the peptide of the present invention may be a peptide having CTL-inducing ability, which comprises an amino acid sequence in which, in the amino acid sequence selected from among SEQ ID NOs: 1, 8, 10, 13, 25, 33 to 35 and 37, the third amino acid from the N terminus is substituted with aspartic acid or glutamic acid, and/or the C-terminal amino acid is substituted with tyrosine. Preferably, the peptide of the present invention may be a peptide having CTL-inducing ability, which consists of an amino acid sequence in which, in the amino acid sequence selected from among SEQ ID NOs: 1, 8, 10, 13, 25, 33 to 35 and 37, the third amino acid from the N terminus is substituted with aspartic acid or glutamic acid, and/or the C-terminal amino acid is substituted with tyrosine. That is, the peptide of the present invention may be a peptide having CTL-inducing ability, which comprises an amino acid sequence in which one or more substitutions selected from (a) and (b) below are introduced into the amino acid sequence selected from among SEQ ID NOs: 1, 8, 10, 13, 25, 33 to 35 and 37:
  (a) the third amino acid from the N terminus is substituted with aspartic acid or glutamic acid; and
  (b) the C-terminal amino acid is substituted with tyrosine.

In a preferred embodiment, the peptide of the present invention may be a peptide having CTL-inducing ability, which consists of an amino acid sequence in which one or more substitutions selected from (a) to (b) above are introduced into the amino acid sequence selected from among SEQ ID NOs: 1, 8, 10, 13, 25, 33 to 35 and 37.

Substitution(s) may be introduced into amino acid(s) not only at the anchor site(s), but also at a position(s) of potential T cell receptor (TCR) recognition site(s) of the peptides. Several research studies have demonstrated that a peptide that has amino acid substitutions, such as CAP1, p53$_{(264-272)}$, Her-2/neu$_{(369-377)}$ or gp100$_{(209-217)}$, may have equal to or better activity than that of the original peptide (Zaremba et al. Cancer Res. 1997, 57, 4570-7; T. K. Hoffmann et al. J Immunol. 2002, 168(3): 1338-47; S. O. Dionne et al. Cancer Immunol immunother. 2003, 52: 199-206; and S. O. Dionne et al. Cancer Immunology, Immunotherapy 2004, 53, 307-14).

The present invention also contemplates that one, two or several amino acids can be added to the N terminus and/or C terminus of the peptides of the present invention (for example, peptides consisting of the amino acid sequence selected from among SEQ ID NOs: 1, 8, 10, 13, 25, 33 to 35 and 37). Such modified peptides that retain CTL-inducing ability are also included in the present invention. For example, when a peptide in which one, two or several amino acids are added to the N terminus and/or C terminus of a peptide consisting of the amino acid sequence of SEQ ID NO: 8 is contacted with an APC(s), it is incorporated into the APC(s) and processed to become a peptide consisting of the amino acid sequence of SEQ ID NO: 8. It can then induce CTLs through presentation on the cell surface of an APC via the antigen presentation pathway. More specifically, peptides of the present invention can be peptides in which one, two or several amino acids are added to either or both of the N terminus and C terminus.

In yet another embodiment of the present invention, peptides consisting of an amino acid sequence which comprises one, two, or several amino acid substitutions in the amino acid sequence referenced by each SEQ ID NO and which further comprises one, two, or several amino acids added to either or both of the N-terminus and the C-terminus of the substitution-bearing amino acid sequence are provided.

When a peptide of the present invention comprises an amino acid substitution, a desired position for the substitution can be, for example, one, two, or three selected from position 2 from the N-terminus, position 3 from the N-terminus, and the C-terminus in the amino acid sequence referenced by SEQ ID NO: 1, 8, 10, 13, 25, 33 to 35 or 37 which is comprised in said peptide of the present invention.

However, when the amino acid sequence of a peptide is identical to a portion of the amino acid sequence of an endogenous or exogenous protein having a different function, side effects such as autoimmune disorders and/or allergic symptoms against specific substances may be induced. Therefore, it is preferable to perform homology searches using available databases to avoid situations in which the amino acid sequence of the peptide matches the amino acid sequence of another protein. When it becomes clear from the homology searches that no peptide exists with as few as 1 or 2 amino acid differences as compared to the objective peptide, the objective peptide can be modified in order to increase its binding affinity with HLA antigens, and/or increase its CTL-inducing ability without danger of such side effects.

Peptides in which one, two or several amino acids of a peptide of the present invention are modified are predicted to be able to retain CTL-inducing ability of the original peptide; however, it is preferable to verify the CTL-inducing ability of the modified peptides. Herein, the "peptide having CTL-inducing ability (CTL inducibility)" refers to a peptide that induces CTLs through APCs stimulated with the peptide. "CTL induction" includes induction of differentiation into CTLs, induction of CTL activation, induction of CTL proliferation, induction of CTL's cytotoxic activity, induction of CTL-mediated dissolution of target cells, and induction of increase of IFN-gamma production of CTLs.

The CTL-inducing ability can be confirmed by inducing and stimulating APCs that retain an HLA antigen (for example, B lymphocytes, macrophages, and dendritic cells) with a peptide, and mixing them with CD8-positive T cells; and then measuring IFN-gamma released by CTLs against the target cells. For the APCs, human peripheral blood mononuclear leukocyte-derived dendritic cells can be preferably used. As a reaction system, transgenic animals generated to express an HLA antigen can be used. Alternatively, for example, the target cells may be radio-labelled with $^{51}$Cr or such, and the cytotoxic activity of the peptide-induced CTLs may be calculated from the radioactivity emitted from the target cells. Alternatively, in the presence of peptide-stimulated APCs, it is possible to evaluate the CTL-inducing ability by measuring the IFN-gamma produced and released by CTLs, and visualizing the inhibition zone on the media using anti-IFN-gamma monoclonal antibodies.

In addition to the modifications above, the peptides of the present invention can be linked to other peptides as long as the resultant linked peptide retains the CTL-inducing ability. An example of an appropriate peptide to be linked with the peptides of the present invention includes a TAA-derived CTL-inducing peptide. Further, the peptides of the present invention can also be linked with each other. Suitable linkers for use in linking peptides are known in the art, and for example, linkers such as AAY (P. M. Daftarian et al., J Trans Med. 2007, 5: 26), AAA, NKRK (SEQ ID NO: 48) (R. P. M. Sutmuller et al., J Immunol. 2000, 165: 7308-15), or K (S. Ota et al., Can Res. 2002, 62, 1471-6; K. S. Kawamura et al., J Immunol. 2002, 168: 5709-15) can be used. Peptides can be linked in various arrangements (for example, catenulate, repeated, etc.), and one can also link three or more peptides.

The peptides of the present invention can also be linked to other substances as long as the resultant linked peptide retains the CTL-inducing ability. Examples of an appropriate substance to be linked with a peptide of the present invention include, for example, a peptide, a lipid, a sugar or sugar chain, an acetyl group, and a naturally-occurring or synthetic polymer. The peptides of the present invention can be modified by glycosylation, side-chain oxidation, phosphorylation or such, as long as their CTL-inducing ability is not impaired. One can also perform such types of modifications to confer additional functions (for example, targeting function and delivery function) or to stabilize the peptide.

For example, to increase the in vivo stability of a peptide, it is known in the art to introduce D-amino acids, amino acid mimetics or non-naturally occurring amino acids, and this concept may also be applied to peptides of the present invention. Peptide stability can be assayed by several methods. For example, stability can be tested by using a peptidase as well as various biological media such as human plasma and serum (see, e.g., Verhoef et al., Eur J Drug Metab Pharmacokin 1986, 11: 291-302).

Further, as stated above, among the modified peptides in which one, two, or several amino acid residues have been substituted, deleted, inserted and/or added, those having equal to or higher activity as compared to original peptides can be screened for or selected. Thus, the present invention also provides methods of screening for or selecting modified peptides that have equal to or higher activity than that of the original peptide. Specifically, the present invention provides a method of screening for a peptide having CTL-inducing ability, wherein the method comprises the steps of:
(a) generating candidate sequences consisting of an amino acid sequence in which one, two, or several amino acid residues are substituted, deleted, inserted and/or added to the original amino acid sequence consisting of the amino acid sequence selected from among SEQ ID NOs: 1, 8, 10, 13, 25, 33 to 35 and 37;
(b) selecting from among the candidate sequences generated in (a), a candidate sequence that does not have a significant homology (sequence identity) with any known human gene product other than CDCA1;
(c) contacting a peptide consisting of the candidate sequence selected in (b) with APCs;
(d) contacting the APCs of (c) with CD8-positive T cells; and
(e) selecting a peptide that has an equal to or higher CTL-inducing ability than that of a peptide consisting of the original amino acid sequence.

In the present invention, all the peptides consisting of SEQ ID NO: 1, 8, 10, 13, 25, 33 to 35 or 37 have an HLA-A01-restrictive CTL-inducing activity. Therefore, in order to select ones with the CTL-inducing ability from their amino-acid-sequence-modified variants, the APCs in step (c) above are desirably cells having HLA-A01.

Herein, the peptide of the present invention is also described as a "CDCA1 peptide(s)" or a "CDCA1 polypeptide(s)".

III. Preparation of Peptides of the Present Invention

Well known techniques can be used to prepare peptides of the present invention. For example, recombinant DNA technology or chemical synthesis can be used to prepare peptides of the present invention. Peptides of the present invention can be synthesized individually, or as longer polypeptides including two or more peptides. Peptides of the present invention can be isolated from host cells or synthesis reaction products after they are produced in the host cells using recombinant DNA technology or after they are chemically synthesized. That is, peptides of the present invention can be purified or isolated so as not to substantially contain other host-cell proteins and fragments thereof, or any other chemical substances.

The peptides of the present invention may contain modifications, such as glycosylation, side chain oxidation, or phosphorylation provided such modifications do not destroy the biological activity of the original peptide. Other illustrative modifications include incorporation of D-amino acids or other amino acid mimetics that may be used, for example, to increase the serum half life of the peptides.

A peptide of the present invention can be obtained through chemical synthesis based on the selected amino acid sequence. Examples of conventional peptide synthesis methods that can be adapted to the synthesis include the methods described in the documents below:

(i) Peptide Synthesis, Interscience, New York, 1966;
(ii) The Proteins, Vol. 2, Academic Press, New York, 1976;
(iii) "Peptide Synthesis" (in Japanese), Maruzen Co., 1975;
(iv) "Basics and Experiment of Peptide Synthesis" (in Japanese), Maruzen Co., 1985;
(v) "Development of Pharmaceuticals" (in Japanese), Continued Vol. 14 (peptide synthesis), Hirokawa, 1991;
(vi) WO99/67288; and
(vii) Barany G. & Merrifield R. B., Peptides Vol. 2, Solid Phase Peptide Synthesis, Academic Press, New York, 1980, 100-118.

Alternatively, the peptides of the present invention can be obtained by adapting any known genetic engineering methods for producing peptides (e.g., Morrison J, J Bacteriology 1977, 132: 349-51; Clark-Curtiss & Curtiss, Wu et al., Methods in Enzymology 1983, 101: 347-62). For example, first, a suitable vector harboring a polynucleotide encoding the peptide of the present invention in an expressible form (e.g., downstream of a regulatory sequence corresponding to a promoter sequence) is prepared and transformed into a suitable host cell. The host cell is then cultured to produce the peptide of the present invention. The peptide of the present invention can also be produced in vitro using an in vitro translation system.

IV. Polynucleotides

The present invention also provides a polynucleotide which encodes any of the peptides of the present invention. These include polynucleotides derived from the naturally occurring CDCA1 gene (e.g., GenBank Accession No. NM_145697 (SEQ ID NO: 44) or GenBank Accession No. NM_031423 (SEQ ID NO: 46)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described above without altering the encoded polypeptide. Such nucleic acid variations are "silent variations", which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (e.g., plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. Exosomes

The present invention further provides intracellular vesicles, referred to as exosomes, that present complexes formed between the peptides of the present invention and HLA antigens on their surface. Exosomes can be prepared, for example, using the methods detailed in JPH11-510507 and WO99/03499, and can be prepared using APCs obtained from patients who are subject to treatment and/or prevention (prophylaxis). The exosomes of the present invention can be inoculated as vaccines, in a fashion similar to the peptides of the present invention.

The type of the HLA antigens included in the above-described complexes must match that of the subject in need of treatment and/or prevention (prophylaxis). For example, HLA-A01 (for example, HLA-A*01:01) is an HLA allele highly frequently observed in Caucasians, and this HLA antigen type is considered to be suitable for treatment in Caucasian patients. Typically in clinical practice, it is possible to select an appropriate peptide that has a high level of binding affinity for a specific HLA antigen or that has CTL-inducing ability by antigen presentation mediated by a specific HLA antigen, by studying in advance the HLA antigen type of the patient in need of treatment.

The exosomes of the present invention present on their surface a complex of a peptide of the present invention and HLA-A01. When the HLA that forms a complex with a peptide of the present invention is HLA-A01, the peptide of the present invention is preferably a peptide having the amino acid sequence selected from among SEQ ID NOs: 1, 8, 10, 13, 25, 33 to 35 and 37 or a modified peptide thereof, and more preferably a peptide consisting of the amino acid sequence selected from among SEQ ID NOs: 1, 8, 10, 13, 25, 33 to 35 and 37 or a modified peptide thereof.

VI. Antigen-Presenting Cells (APCs)

The present invention further provides APCs that present on their surface complexes formed between HLA antigens and peptides of the present invention. Alternatively, the present invention provides APCs having on their cell surface complexes formed between HLA antigens and peptides of the present invention. The APCs of the present invention can be isolated APCs. When used in the context of cells (APCs, CTLs, etc.), the term "isolated" means that the cells are separated from another type of cells. The APCs of the present invention may be APCs induced from APCs derived from the patient to be subjected to treatment and/or prevention (prophylaxis), and can be administered as a vaccine by themselves or in combination with other drugs including a peptide(s), an exosome(s) or a CTL(s) of the present invention.

The APCs of the present invention are not limited to specific types of cells, and include cells known to present proteinaceous antigens on their cell surface so as to be recognized by lymphocytes, for example, dendritic cells (DCs), Langerhans cells, macrophages, B cells, and activated T cells. Since DC is a representative APC that has the strongest CTL-inducing activity among APCs, DCs can be preferably used as the APCs of the present invention.

For example, APCs of the present invention can be obtained by inducing DCs from peripheral blood monocytes and then stimulating them in vitro, ex vivo or in vivo with the peptides of the present invention. When the peptide of the present invention is administered to a subject, APCs presenting the peptide of the present invention are induced in the body of the subject. Therefore, after the peptides of the present invention are administered to a subject, the APCs of the present invention can be obtained by collecting APCs from the subject.

Alternatively, the APCs of the present invention can be obtained by contacting APCs collected from a subject with a peptide of the present invention.

In order to induce an immune response against CDCA1-expressing cancer cells in a subject, the APCs of the present invention can be administered to the subject by themselves or in combination with other drugs including peptide(s), exosome(s) or CTL(s) of the present invention. For example, the ex vivo administration can comprise the following steps of:

(a) collecting APCs from a first subject;
(b) contacting the APCs of step (a) with a peptide; and
(c) administering the APCs of step (b) to a second subject.

The first subject and the second subject may be the same individual, or may be different individuals. When the first subject and the second subject are different individuals, it is preferable that the HLAs of the first subject and the second subject are of the same type. The APC obtained in step (b) above can be a vaccine for cancer treatment and/or prevention (prophylaxis).

The APCs of the present invention obtained by a method such as described above have CTL-inducing ability. The term "CTL-inducing ability (CTL inducibility)" used in the context of an APC(s) refers to the ability of the APC to be able to induce a CTL(s) when placed in contact with a CD8-positive T cell(s). The CTL(s) induced by the APC of the present invention is a CTL(s) specific to CDCA1 and demonstrates a specific cytotoxic activity against CDCA1-expressing cells.

In addition to the above-described methods, the APCs of the present invention can be prepared by introducing a polynucleotide encoding a peptide of the present invention into APCs in vitro. The polynucleotide to be introduced can be in the form of DNA or RNA. The method of introduction is not particularly limited, and examples thereof include various methods conventionally performed in the art such as lipofection, electroporation and the calcium phosphate method. More specifically, methods described in Cancer Res 1996, 56: 5672-7; J Immunol 1998, 161: 5607-13; J Exp Med 1996, 184: 465-72; and JP2000-509281 can be used. By introducing a polynucleotide encoding a peptide of the present invention into an APC, the polynucleotide is transcribed and translated in the cell, and then the produced peptide is processed by MHC Class I and proceeds through a presentation pathway to present the peptide of the present invention on the cell surface of the APC.

In a preferred embodiment, the APC of the present invention is an APC that presents on its cell surface a complex formed between HLA-A01 (more preferably HLA-A*01:01) and a peptide of the present invention. When the HLA that forms a complex with a peptide of the present invention is HLA-A01, the peptide of the present invention is preferably a peptide having the amino acid sequence selected from among SEQ ID NOs: 1, 8, 10, 13, 25, 33 to 35 and 37 or a modified peptide thereof, and more preferably a peptide consisting of the amino sequence selected from among SEQ ID NOs: 1, 8, 10, 13, 25, 33 to 35 and 37.

The APC(s) of the present invention is preferably an APC(s) induced by a method comprising a step described (a) or (b) below:

(a) contacting an APC(s) expressing HLA-A01 (more preferably HLA-A*01:01) with a peptide of the present invention; or
(b) introducing a polynucleotide encoding a peptide of the present invention into an APC(s) expressing HLA-A01 (more preferably HLA-A*01:01).

The peptide of the present invention to be contacted with the HLA-A01-expressing APC(s) is preferably a peptide having the amino acid sequence selected from among SEQ ID NOs: 1, 8, 10, 13, 25, 33 to 35 and 37 or a modified peptide thereof, and more preferably a peptide consisting of the amino acid sequence selected from among SEQ ID NOs: 1, 8, 10, 13, 25, 33 to 35 and 37.

The present invention provides use of a peptide of the present invention for the manufacture of a pharmaceutical composition that induces an APC(s) having CTL-inducing ability. In addition, the present invention provides a method or process of manufacturing a pharmaceutical composition that induces an APC(s) having CTL-inducing ability. Further, the present invention provides a peptide of the present invention for inducing an APC(s) having CTL-inducing ability.

VII. Cytotoxic T Lymphocytes (CTLs)

The CTL induced by a peptide of the present invention can be used as a vaccine in a similar manner to the peptide of the present invention since it enhances an immune response targeting CDCA1-expressing cancer cell in vivo. Thus, the present invention provides CTLs that are induced or activated by a peptide of the present invention. The CTLs of the present invention are CTLs that target a peptide of the present invention, and are capable of binding to a complex of a peptide of the present invention and an HLA antigen. Binding of a CTL to the complex is mediated via a T cell receptor (TCR) present on the cell surface of the CTL. The CTLs of the present invention can be isolated CTLs.

The CTLs of the present invention can be obtained by (1) administering a peptide of the present invention to a subject, (2) stimulating APCs and CD8-positive T cells, or peripheral blood mononuclear cells (PBMCs) derived from a subject with a peptide of the present invention in vitro, (3) contacting in vitro CD8-positive T cells or PBMCs with APCs or exosomes that present on their surface a complex of an HLA antigen and a peptide of the present invention, or (4) introducing into CD8-positive T cells a vector comprising a polynucleotide encoding each subunit of a T cell receptor (TCR) capable of binding to a peptide of the present invention presented on cell surface via an HLA antigen. The exosomes and APCs used in the method of (2) or (3) above can be prepared by methods described in the "V. Exosomes" and "VI. Antigen-presenting cells (APCs)" sections, respectively, and the details of the method of (4) above will be described in the "VIII. T cell receptors (TCRs)" section.

The CTLs of the present invention can be administered by themselves to patients who are subject to treatment and/or prevention (prophylaxis), or in combination with other drugs including peptide(s), APC(s) or exosome(s) of the present invention for the purpose of regulating effects. Further, the CTLs of the present invention can be CTLs induced from CD8-positive T cells derived from the patients who are subject to administration of the CTLs. The CTLs of the present invention act specifically on target cells that present the peptides of the present invention, for example, the same peptides used to induce the CTLs of the present invention. The target cells may be cells that endogenously express CDCA1, such as cancer cells, or cells transfected with the CDCA1 gene. Cells that present a peptide of the present invention on their cell surface due to stimulation by the peptide can become a target of attack by the CTLs of the present invention. The cells targeted by the CTLs of the present invention are preferably cells that are positive for HLA-A01 (more preferably HLA-A*01:01).

In a preferred embodiment, the CTLs of the present invention target specifically cells that express both HLA-A01 (more preferably HLA-A*01:01) and CDCA1. Herein, that the CTL "targets" cells refers to CTL recognition of cells that present on their cell surface a complex of HLA and a peptide of the present invention and demonstration of a cytotoxic activity against the cells. Further, "specifically target" refers to that the CTLs demonstrate a cytotoxic activity against those cells, but do not show a damaging activity to other cells. The expression "recognize cells" used in the context of CTLs refers to binding to a complex of HLA and a peptide of the present invention presented on cell surface via its TCR, and demonstrating a specific cytotoxic activity against the cell. Therefore, the CTLs of the present invention are preferably CTLs that can bind via TCR to a complex formed between HLA-A01 (more preferably HLA-A*01:01) and a peptide of the present invention presented on cell surface.

Furthermore, the CTLs of the present invention are preferably CTLs induced by a method comprising a step described in (a) or (b) below:
  (a) contacting in vitro CD8-positive T cells with APCs or exosomes that present on their surface a complex of HLA-A01 (more preferably HLA-A*01:01) and a peptide of the present invention; or
  (b) introducing into CD8-positive T cells a polynucleotide encoding each subunit of a TCR capable of binding to a peptide of the present invention presented on cell surface by HLA-A01 (more preferably HLA-A*01:01).

VIII. T Cell Receptors (TCRs)

The present invention also provides compositions comprising a polynucleotide encoding each subunit of a TCR capable of binding to a peptide of the present invention presented on cell surface by an HLA antigen, and methods of using the same. The polynucleotide confers CD8-positive T cells with specificity against CDCA1-expressing cancer cells through expression of a TCR on cell surface capable of binding to a peptide of the present invention presented on cell surface by an HLA antigen. Polynucleotides encoding an alpha chain(s) and a beta chain(s) can be identified as the TCR subunit of the CTL induced by a peptide of the present invention by using known methods in the art (WO2007/032255 and Morgan et al., J Immunol, 2003, 171, 3288). For example, PCR methods are preferred for TCR analysis. PCR primers for analysis may be, for example, 5'-R Primer (5'-gtctaccaggcattcgcttcat-3') (SEQ ID NO: 40) as a 5' side primer; and 3-TRa-C Primer (5'-tcagctggaccacagccgcagcgt-3') (SEQ ID NO: 41) specific to TCR-alpha-chain C-region, 3-TRb-C1 Primer (5'-tcagaaatcctttctcttgac-3') (SEQ ID NO: 42) specific to TCR-beta-chain C1-region, or 3-TRb-C2 Primer (5'-ctagcctctggaatcctttctctt-3') (SEQ ID NO: 43) specific to TCR-beta-chain C2-region as 3' side primers, but are not limited thereto. The TCRs formed by introducing the identified polynucleotides into CD8-positive T cells can bind with high binding affinity to the target cells that present a peptide of the present invention, and mediates efficient killing of the target cells presenting a peptide of the present invention in vivo and in vitro.

A polynucleotide encoding each TCR subunit can be incorporated into an appropriate vector, for example, retrovirus vector. These vectors are well known in the art. The polynucleotide or a vector comprising thereof in an expressible form can be introduced into a CD8-positive T cell, for example, a CD8-positive T cell derived from a patient. The present invention provides off-the-shelf compositions that allow rapid and easy production of modified T cells that have superior cancer cell-killing properties by rapid modification of the patient's own T cells (or T cells derived from another subject).

Herein, a specific TCR is a TCR that can confer a specific cytotoxic activity against target cells by specifically recognizing a complex of a peptide of the present invention and an HLA antigen presented on the surface of the target cell when the TCR is present on the surface of a CD8-positive T cell. Specific recognition of the above-described complex can be confirmed by any known method, and preferable examples thereof include HLA multimer staining analysis using HLA molecules and peptides of the present invention and ELISPOT assay methods. Specific TCR-mediated recognition of target cell by T cell introduced with the above-described polynucleotide and signal transduction in the cell can be confirmed by carrying out an ELISPOT assay. When the above-described TCR is present on the surface of a CD8-positive T cell, whether the TCR can confer a target cell-specific cytotoxic activity against the CD8-positive T cell can also be confirmed by known methods. Preferable methods include, for example, measuring the cytotoxic activity against target cells by a chrome release assay method or such.

The present invention provides, in the context of HLA-A01, CTLs prepared by transforming CD8-positive T cells with a polynucleotide encoding each subunit of TCR that binds to, for example, a peptide having the amino acid sequence selected from among SEQ ID NOs: 1, 8, 10, 13, 25, 33 to 35 and 37.

The transformed CTLs are capable of homing in vivo and may be propagated by a well-known in vitro culturing method (for example, Kawakami et al., J Immunol., 1989, 142, 3452-61). The CTLs of the present invention can be used to form an immunogenic composition useful for disease treatment or prevention (prophylaxis) in a patient in need of treatment or prevention (prophylaxis) (the contents are incorporated herein for reference WO2006/031221).

IX. Pharmaceutical Compositions

The present invention further provides compositions or pharmaceutical compositions, comprising at least one active ingredient selected from below:
(a) a peptide of the present invention;
(b) a polynucleotide encoding a peptide of the present invention in an expressible form;
(c) an APC of the present invention;
(d) an exosome of the present invention; and
(e) a CTL of the present invention.

The pharmaceutical compositions of the present invention can comprise as needed a carrier(s), an excipient(s) or such commonly used in pharmaceuticals without particular limitations, in addition to the active ingredient(s) described above. An example of a carrier that can be used in a pharmaceutical composition of the present invention includes sterilized water, physiological saline, phosphate buffer, culture fluid and such. Therefore, the present invention also provides pharmaceutical compositions, comprising at least one active ingredient selected from (a) to (e) below and a pharmaceutically acceptable carrier:
(a) a peptide of the present invention;
(b) a polynucleotide encoding a peptide of the present invention in an expressible form;
(c) an APC of the present invention;
(d) an exosome of the present invention; and
(e) a CTL of the present invention.

Further, the pharmaceutical compositions of the present invention can comprise, as needed, stabilizers, suspensions, preservatives, surfactants, solubilizing agents, pH adjusters, aggregation inhibitors and such.

The CDCA1 expression significantly up-regulates in cancer cells compared with normal tissues. Thus, a peptide of the present invention or a polynucleotide encoding the peptide can be used to treat and/or prevent cancer, and/or prevent postoperative recurrence thereof. Therefore, the present invention provides pharmaceutical compositions for treating and/or preventing cancer, and/or preventing postoperative recurrence thereof, comprising one or more types of peptides or polynucleotides of the present invention as an active ingredient. Alternatively, the peptides of the present invention can be made to be presented on the surface of exosomes or APCs for use as pharmaceutical compositions. In addition, CTLs of the present invention targeting any one of the peptides of the present invention can also be used as an active ingredient of the pharmaceutical compositions of the present invention. The pharmaceutical compositions of the present invention may comprise a therapeutically effective amount or a pharmaceutically effective amount of the above-described active ingredient.

The pharmaceutical compositions of the present invention may also be used as a vaccine. In the context of the present invention, the term "vaccine" (also called "immunogenic composition") refers to a composition that has a function of inducing an immune response that leads to antitumor action when inoculated into an animal. Thus, a pharmaceutical composition of the present invention can be used to induce an immune response that leads to antitumor action. The immune response induced by a peptide, a polynucleotide, an APC, a CTL and a pharmaceutical composition of the present invention is not particularly limited as long as it is an immune response that leads to antitumor action, and examples include induction of cancer cell-specific CTLs and induction of cancer cell-specific cytotoxic activity.

The pharmaceutical compositions of the present invention can be used to treat and/or prevent cancer, and/or prevent postoperative recurrence thereof in human subjects or patients. The pharmaceutical compositions of the present invention can be used preferably to a subject positive for HLA-A01. Further, the pharmaceutical compositions of the present invention can be used preferably to treat and/or prevent cancers expressing HLA-A01 and CDCA1, and/or prevent postoperative recurrence thereof.

In another embodiment, the present invention provides use of an active ingredient selected from below in the manufacture of a pharmaceutical composition for treating or preventing cancer expressing HLA-A01 and CDCA1:
(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides an active ingredient selected from below for use in treating or preventing cancer expressing HLA-A01 and CDCA1:
(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides a method or process for manufacturing a pharmaceutical composition for treating or preventing cancer expressing HLA-A01 and CDCA1, wherein the method or process comprises a step of formulating at least one active ingredient selected from below with a pharmaceutically or physiologically acceptable carrier:
(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In another embodiment, the present invention further provides a method or process for manufacturing a pharmaceutical composition for treating or preventing cancer expressing HLA-A01 and CDCA1, wherein the method or process comprises a step of mixing an active ingredient selected from below with a pharmaceutically or physiologically acceptable carrier:
(a) a peptide of the present invention;
(b) a polynucleotide encoding a peptide of the present invention in an expressible form;
(c) an APC that presents a peptide of the present invention on its surface;

(d) an exosome that presents a peptide of the present invention on its surface; and (e) a CTL of the present invention.

In another embodiment, the present invention further provides a method for treating or preventing cancer expressing HLA-A01 and CDCA1, which comprises a step of administering to a subject at least one active ingredient selected from below:

(a) a peptide of the present invention;

(b) a polynucleotide encoding a peptide of the present invention in an expressible form;

(c) an APC that presents a peptide of the present invention on its surface;

(d) an exosome that presents a peptide of the present invention on its surface; and (e) a CTL of the present invention.

In the present invention, peptides having the amino acid sequence selected from among SEQ ID NOs: 1, 8, 10, 13, 25, 33 to 35 and 37 are identified as HLA-A01-restricted epitope peptides that can induce a potent and specific immune response. Therefore, pharmaceutical compositions of the present invention comprising at least one peptide having the amino acid sequence selected from among SEQ ID NOs: 1, 8, 10, 13, 25, 33 to 35 and 37 are suitable particularly for administration to a subject having HLA-A01 (for example, HLA-A*01:01) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 1, 8, 10, 13, 25, 33 to 35 and 37 are suitable for administration to subjects having HLA-A01 (i.e., HLA-A01-positive subjects). In a more preferred embodiment, the pharmaceutical composition of the present invention is a pharmaceutical composition that comprises a peptide having the amino acid sequence of SEQ ID NO: 8.

Cancers to be treated and/or prevented by pharmaceutical compositions of the present invention are not particularly limited as long as they are cancers that express CDCA1, and include various cancers, bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue tumor, colon cancer and such.

In addition to the active ingredients described above, the pharmaceutical compositions of the present invention can comprise the other peptides that have the ability to induce CTLs against cancer cells (for example, the other TAA-derived CTL-inducing peptides), the other polynucleotides encoding the other peptides, the other cells that present the other peptides, or such.

The pharmaceutical compositions of the present invention may also optionally comprise the other therapeutic substances as an active ingredient, as long as they do not inhibit the anti-tumor effects of the above-described active ingredients such as peptides of the present invention. For example, the pharmaceutical compositions of the present invention may optionally comprise anti-inflammatory compositions, analgesics, chemotherapeutics and the like. In addition to including the other therapeutic substances to a pharmaceutical composition of the present invention itself, one can also administer the pharmaceutical composition of the present invention sequentially or concurrently with one or more other pharmaceutical compositions. The dose of the pharmaceutical composition of the present invention and the other pharmaceutical compositions depend on, for example, the type of pharmaceutical composition used and the disease being treated, as well as the scheduling and routes of administration.

It should be understood that in consideration of the formulation type, the pharmaceutical composition of the present invention may include other components conventional in the art, in addition to the ingredients specifically mentioned herein.

The present invention also provides articles of manufacture or kits that comprise a pharmaceutical composition of the present invention. The articles of manufacture or kits of the present invention can include a container that houses the pharmaceutical composition of the present invention. An example of an appropriate container includes a bottle, a vial or a test tube, but is not limited thereto. The container may be formed of various materials such as glass or plastic. A label may be attached to the container, and the disease or disease state to which the pharmaceutical composition of the present invention should be used may be described in the label. The label may also indicate directions for administration and such.

The articles of manufacture or kits of the present invention may further comprise a second container that houses pharmaceutically acceptable diluents optionally, in addition to the container that houses the pharmaceutical composition of the present invention. The articles of manufacture or kits of the present invention may further comprise the other materials desirable from a commercial standpoint and the user's perspective, such as the other buffers, diluents, filters, injection needles, syringes, package inserts with instructions for use.

As needed, the pharmaceutical composition of the present invention can be provided in a pack or dispenser device that can contain one or more units of dosage forms containing active ingredients. The pack can include, for example, a metallic foil or a plastic foil such as a blister pack. Instructions for administration can be attached to the pack or dispenser device.

(1) Pharmaceutical Compositions Comprising Peptide(s) as an Active Ingredient

The pharmaceutical composition comprising a peptide of the present invention can be formulated by conventional formulation methods as needed. The pharmaceutical compositions of the present invention may comprise as needed in addition to the peptide of the present invention, carriers, excipients and such commonly used in pharmaceuticals without particular limitations. Examples of carriers that can be used in pharmaceutical compositions of the present invention include sterilized water (for example, water for injection), physiological saline, phosphate buffer, phosphate buffered saline, Tris buffered saline, 0.3% glycine, culture fluid, and such. Further, the pharmaceutical compositions of the present invention may comprise as needed stabilizers, suspensions, preservatives, surfactants, solubilizing agents, pH adjusters, aggregation inhibitors, and such. The pharmaceutical compositions of the present invention can induce specific immunity against CDCA1-expressing cancer cells, and thus can be applied for the purpose of cancer treatment or prevention (prophylaxis).

For example, the pharmaceutical compositions of the present invention can be prepared by dissolving in pharmaceutically or physiologically acceptable water-soluble carriers such as sterilized water (for example, water for injection), physiological saline, phosphate buffer, phosphate buffered saline, and Tris buffered saline and adding, as needed, stabilizers, suspensions, preservatives, surfactants, solubilizing agents, pH adjusters, aggregation inhibitors and such, and then sterilizing the peptide solution. The method of sterilizing a peptide solution is not particularly limited, and is preferably carried out by filtration sterilization. Filtration sterilization can be performed using, for example, a filtration sterilization filter of 0.22 micro-m or less in pore diameter. The filtration-sterilized peptide solution can be administered to a subject, for example, as an injection, without being limited thereto. The pharmaceutical compositions of the present invention may be prepared as a freeze-dried formulation by freeze-drying the above-described peptide solution. The freeze-dried formulation can be prepared by filling the peptide solution prepared as described above into an appropriate container such as an ampule, a vial or a plastic container, followed by freeze drying and encapsulation into the container with a wash-sterilized rubber plug or such after pressure recovery. The freeze-dried formulation can be administered to a subject after it is re-dissolved in pharmaceutically or physiologically acceptable water-soluble carriers such as sterilized water (for example, water for injection), physiological saline, phosphate buffer, phosphate buffered saline, Tris buffered saline and such before administration. Preferred examples of pharmaceutical compositions of the present invention include injections of such a filtration-sterilized peptide solution, and freeze-dried formulations that result from freeze-drying the peptide solution. The present invention further encompasses kits comprising such a freeze-dried formulation and re-dissolving solution. The present invention also encompasses kits comprising a container that houses the freeze-dried formulation, which is a pharmaceutical composition of the present invention, and a container that stores a re-dissolving solution thereof.

The pharmaceutical compositions of the present invention can comprise a combination of two or more types of the peptides of the present invention. The combination of peptides can take a cocktail form of mixed peptides, or can be conjugated with each other using standard techniques. For example, peptides can be chemically linked or expressed as single fusion polypeptide sequences. By administering a peptide of the present invention, the peptide is presented on APCs by an HLA antigen at a high density, and then subsequently CTLs that react specifically to a complex formed between the presented peptide and the HLA antigen are induced. Alternatively, APCs (for example, DCs) are removed from a subject, and subsequently stimulated with peptides of the present invention to obtain APCs that present any of the peptides of the present invention on their cell surface. These APCs are re-administered to a subject to induce CTLs in the subject, and as a result, the aggressiveness towards CDCA1-expressing cancer cells can be increased.

The pharmaceutical compositions of the present invention may also comprise an adjuvant known for effectively establishing cellular immunity. An adjuvant refers to a compound that enhances the immune response against an antigen that has immunological activity when administered together (or successively) with the antigen. Known adjuvants described in literatures, for example, Clin Microbiol Rev 1994, 7: 277-89, can be used. Examples of a suitable adjuvant include aluminum salts (aluminum phosphate, aluminum hydroxide, aluminum oxyhydroxide and such), alum, cholera toxin, *Salmonella* toxin, Incomplete Freund's adjuvant (IFA), Complete Freund's adjuvant (CFA), ISCOMatrix, GM-CSF and other immunostimulatory cytokines, oligodeoxynucleotide containing the CpG motif (CpG7909 and such), oil-in-water emulsions, Saponin or its derivatives (QS21 and such), lipopolysaccharide such as Lipid A or its derivatives (MPL, RC529, GLA, E6020 and such), lipopeptides, lactoferrin, flagellin, double-stranded RNA or its derivatives (poli IC and such), bacterial DNA, imidazoquinolines (Imiquimod, R848 and such), C-type lectin ligand (trehalose-6,6'-dibehenate (TDB) and such), CD1d ligand (alpha-galactosylceramide and such), squalene emulsions (MF59, AS03, AF03 and such), PLGA, and such, without being limited thereto. These adjuvants can usually be mixed with an antigen having immunological activity (i.e., the peptide of the present invention) in an amount effective for enhancing or strengthening the antigen's immunogenicity. The adjuvant may be contained in another container separate from the pharmaceutical composition comprising a peptide of the present invention in the kits comprising the pharmaceutical composition of the present invention. In this case, the adjuvant and the pharmaceutical composition may be administered to a subject in succession, or mixed together immediately before administration to a subject. Such kits comprising a pharmaceutical composition comprising a peptide of the present invention and an adjuvant are also provided by the present invention. When the pharmaceutical composition of the present invention is a freeze-dried formulation, the kit can further comprise a re-dissolving solution. Further, the present invention provides kits comprising a container that houses a pharmaceutical composition of the present invention and a container that stores an adjuvant. The kit can further comprise as needed a container that stores the re-dissolving solution.

When an oil adjuvant is used as an adjuvant, the pharmaceutical composition of the present invention may be prepared as an emulsion. Emulsions can be prepared, for example, by mixing and stirring the peptide solution prepared as described above and an oil adjuvant. The peptide solution may be one that has been re-dissolved after freeze-drying. The emulsion may be either of the W/O-type emulsion and O/W-type emulsion, and the W/O-type emulsion is preferred for obtaining a high immune response-enhancing effect. IFA can be preferably used as an oil adjuvant, without being limited thereto. Preparation of an emulsion can be carried out immediately before administration to a subject, and in this case, the pharmaceutical composition of the present invention may be provided as a kit comprising the peptide solution of the present invention and an oil adjuvant. When the pharmaceutical composition of the present invention is a freeze-dried formulation, the kit can further comprise a re-dissolving solution.

Further, the pharmaceutical composition of the present invention may be a liposome formulation within which a peptide of the present invention is encapsulated, a granular formulation in which a peptide is bound to beads with several micrometers in diameter, or a formulation in which a lipid is bound to a peptide.

In another embodiment of the present invention, the peptide of the present invention may also be administered in the form of a pharmaceutically acceptable salt. Preferred examples of salts include salts with alkali metals (lithium, potassium, sodium and such), salts with alkaline-earth metals (calcium, magnesium and such), salts with other metals (copper, iron, zinc, manganese and such), salts with organic bases, salts with amines, salts with organic acids (acetic acid, formic acid, propionic acid, fumaric acid, maleic acid, succinic acid, tartaric acid, citric acid, malic acid, oxalic acid, benzoic acid, methanesulfonic acid and such), and salts with inorganic acids (hydrochloric acid, phosphoric acid, hydrobromic acid, sulfuric acid, nitric acid and such). Therefore, pharmaceutical compositions comprising a pharmaceutically acceptable salt of a peptide of the present invention are also encompassed by the present invention. Further, the "peptide of the present invention" also encompasses, in addition to the free peptide, pharmaceutically acceptable salts thereof.

In some embodiments, the pharmaceutical compositions of the present invention may further include a component which primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, E. coli lipoproteins, such as tripalmitoyl-S-glycerylcysteinyl-seryl-serine (P3CSS) can be used to prime CTLs when covalently attached to an appropriate peptide (see, e.g., Deres et al., Nature 1989, 342: 561-4).

Examples of methods for administering the peptides or pharmaceutical compositions of the present invention include oral, epidermal, subcutaneous, intramuscular, intraosseous, peritoneal, and intravenous injections, as well as systemic administration or local administration to the vicinity of the targeted sites, but are not limited thereto. A preferred administration method includes subcutaneous injection to the vicinity of lymph nodes such as the armpit or groin. The administration can be performed by single administration or boosted by multiple administrations. The peptides of the present invention can be administered to a subject in a therapeutically or pharmaceutically effective amount for treating cancer or in a therapeutically or pharmaceutically effective amount for inducing immunity (more specifically CTLs) against CDCA1-expressing cancer cells. The dose of the peptides of the present invention can be appropriately adjusted according to the disease to be treated, the patient's age and weight, the method of administration and such. For each of the peptides of the present invention, the dose is usually 0.001 mg-1000 mg, for example, 0.01 mg-100 mg, for example, 0.1 mg-30 mg, for example, 0.1 mg-10 mg, for example, 0.5 mg-5 mg. The dosing interval can be once every several days to several months, and for example, the dosing can be done in a once-per-week interval. A skilled artisan can appropriately select a suitable dosage.

In a preferred embodiment, the pharmaceutical compositions of the present invention comprise a therapeutically effective amount of a peptide of the present invention and a pharmaceutically or physiologically acceptable carrier. In another embodiment, the pharmaceutical compositions of the present invention comprise a therapeutically effective amount of a peptide of the present invention, a pharmaceutically or physiologically acceptable carrier, and an adjuvant. The pharmaceutical compositions of the present invention can comprise 0.001 mg-1000 mg, preferably 0.01 mg-100 mg, more preferably 0.1 mg-30 mg, even more preferably 0.1 mg-10 mg, for example, 0.5 mg-5 mg of a peptide of the present invention.

When a pharmaceutical composition of the present invention is an injection, it can comprise a peptide of the present invention at a concentration of 0.001 mg/ml-1000 mg/ml, preferably 0.01 mg/ml-100 mg/ml, more preferably 0.1 mg/ml-30 mg/ml, even more preferably 0.1 mg/ml-10 mg/ml, for example, 0.5 mg/ml-5 mg/ml. In this case, for example, 0.1 to 5 ml, preferably 0.5 ml to 2 ml of the pharmaceutical composition of the present invention can be administered to a subject by injection.

Further, the present invention provides methods of treating and/or preventing cancer and/or preventing postoperative recurrence thereof, which comprise administering to a subject a therapeutically effective amount of a peptide of the present invention or a pharmaceutical composition of the present invention. As described above, the peptides of the present invention can be administered to a subject in a single dose of usually 0.001 mg-1000 mg, for example, 0.01 mg-100 mg, for example, 0.1 mg-30 mg, for example, 0.1 mg-10 mg, or for example, 0.5 mg-5 mg. In a preferred embodiment, the peptides of the present invention are administered to a subject together with an adjuvant. Further, the dosing interval can be once every several days to several months, preferably once every several days to every month, for example, once every week or once every two weeks.

The CDCA1 peptides of the invention carry an HLA-A01-restrictive CTL-inducing activity. Accordingly, their therapeutic effect is also effective in HLA-A01-positive subjects. Thus, in a preferred embodiment of the present invention, an HLA-A01-positive subject can be selected in advance, before the administration of a CDCA1 peptide of the present invention. Furthermore, since the therapeutic effect of the CDCA1 of the present invention is CDCA1-specific, it is a desirable condition that cancer in a subject is expressing CDCA1. That is, the methods of treating cancer of the present invention can comprise the step of selecting an HLA-A01-positive subject and the step of selecting a subject having cancer expressing CDCA1, before the administration of the CDCA1 peptide.

(2) Pharmaceutical Compositions Containing Polynucleotides as the Active Ingredient The pharmaceutical compositions of the present invention can also contain polynucleotides encoding the peptides of the present invention in an expressible form. Herein, the phrase "in an expressible form" means that the polynucleotide, when introduced into a cell, will be expressed as a peptide of the present invention. In an exemplified embodiment, the sequence of the polynucleotide of the present invention includes regulatory elements necessary for expression of the peptide of the present invention. The polynucleotide(s) of the present invention can be equipped with a sequence necessary to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859, 5,589, 466, 5,804,566, 5,739,118, 5,736,524, 5,679,647; and WO98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. For example, as a vector to express the peptide of the present invention, vaccinia virus can be used. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide of the present invention into a patient can be either direct, in which case the patient can be directly exposed to a vector harboring the polynucleotide of the present invention, or indirect, in which case, cells are first transformed with the vector harboring the polynucleotide of the present invention in vitro, then the cells are transplanted into the patient. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215. Methods commonly known in the art of recombinant DNA technology which can also be used for the present invention are described in Ausubel et al., Current Protocols in Molecular Biology, John Wiley & Sons, N.Y., 1993; and Krieger, Gene Transfer and Expression, A Laboratory Manual, Stockton Press, N.Y., 1990. Administration methods may be oral, intradermal, subcutaneous, or intravenous injection, and such. A systemic administration or a local administration to the vicinity of the targeted sites is used. The administration can be performed by single administration or boosted by multiple administrations. The polynucleotides of the present invention can be administered to a subject in a therapeutically or pharmaceutically effective dose for inducing immunity (more specifically CTLs) against CDCA1-expressing cancer cells, or in a therapeutically or pharmaceutically effective dose for treating cancer. The dose of a polynucleotide in a suitable carrier or the dose of a polynucleotide in cells transformed with a polynucleotide encoding a peptide of the present invention can be appropriately adjusted according to the disease to be treated, the patient's age and weight, the method of administration and such, and this may be usually 0.001 mg-1000 mg, for example, 0.01 mg-100 mg, for example, 0.1 mg-30 mg, for example, 0.1 mg-10 mg, or for example, 0.5 mg-5 mg. The dosing interval can be once every several days to several months, and for example, the dosing can be done in a once-per-week interval. A skilled artisan can appropriately select a suitable dosage.

X. Methods of Using Peptides, Exosomes, APCs and CTLs

The peptides and polynucleotides of the present invention can be used to induce APCs and CTLs. CTLs can also be induced using the exosomes and APCs of the present invention. The peptides, polynucleotides, exosomes, and APCs can be used in combination with any other compound(s) as long as their CTL-inducing ability is not inhibited. Therefore, CTLs of the present invention can be induced using a pharmaceutical composition comprising any of the peptides, polynucleotides, APCs and exosomes of the present invention. Further, APCs of the present invention can be induced using a pharmaceutical composition comprising a peptide or polynucleotide of the present invention.

(1) Methods of Inducing APCs

The present invention provides methods of inducing APCs having CTL-inducing ability, using a peptide(s) or polynucleotide(s) of the present invention.

The methods of the present invention comprise a step of contacting an APC with a peptide of the present invention in vitro, ex vivo, or in vivo. For example, a method of contacting APCs with the peptide ex vivo may comprise the steps below:
  (a) collecting APCs from a subject; and
  (b) contacting the APCs of step (a) with a peptide of the present invention.

The above-described APCs are not limited to a particular type of cell, and DCs, Langerhans cells, macrophages, B cells, and activated T cells, which are known to present a proteinaceous antigen on their cell surface to be recognized by lymphocytes, can be used. DCs have the most potent CTL-inducing ability among APCs, and thus it is preferable to use DCs.

Any peptides of the present invention can be used by themselves or in combination with other peptides of the present invention. Further, peptides of the present invention can be used in combination with other CTL-inducing peptides (for example, other TAA-derived CTL-inducing peptides).

Meanwhile, when a peptide of the present invention is administered to a subject, APCs are contacted with the peptide in vivo, and as a result, APCs having a high CTL-inducing ability are induced in the body of the subject. Therefore, the methods of the present invention may comprise a step of administering a peptide of the present invention to a subject. Similarly, when a polynucleotide of the present invention is administered to a subject in an expressible form, a peptide of the present invention is expressed in vivo, the expressed peptide is contacted with APCs in vivo, and as a result APCs having a high CTL-inducing ability are induced in the body of the subject. Therefore, the present invention may also comprise a step of administering a polynucleotide of the present invention to a subject.

In order to induce APCs having CTL-inducing ability, the present invention may comprise a step of introducing a polynucleotide of the present invention into APCs. For example, the method may comprise the steps below:
  (a) collecting APCs from a subject; and
  (b) introducing a polynucleotide encoding a peptide of the present invention into the APCs of step (a).
Step (b) can be performed as described in the above "VI. Antigen-presenting cells (APCs)" section.

Thus, in one embodiment, the present invention provides a method of inducing APCs having CTL-inducing ability, which comprises the step (a) or (b) below:
  (a) contacting APCs with a peptide of the present invention; or
  (b) introducing a polynucleotide encoding a peptide of the present invention into APCs.

Furthermore, the present invention provides a method of preparing APCs having CTL-inducing ability, which comprises the step (a) or (b) below:
  (a) contacting APCs with a peptide of the present invention; or
  (b) introducing a polynucleotide encoding a peptide of the present invention into APCs.

The above-described methods can be performed in vitro, ex vivo, or in vivo, and it is preferable to perform them in vitro or ex vivo. APCs used in the above-described methods may be derived from a subject scheduled for administration of the induced APCs, or they may be derived from a different subject. When APCs derived from a subject (donor) different from the subject scheduled for administration are used, the subject of administration and the donor must have the identical HLA type. In the methods of the present invention, when a peptide having the amino acid sequence selected from among SEQ ID NOs: 1, 8, 10, 13, 25, 33 to 35 and 37 or a modified peptide thereof is used as a peptide of the present invention, the HLA type is preferably HLA-A01 (more preferably HLA-A*01:01) in both the subject of administration and the donor. Alternatively, APCs used in the above-described methods are preferably APCs that express HLA-A01 (more preferably HLA-A*01:01). The APCs can be prepared using known methods from PBMCs after PBMCs are separated from blood collected from a donor by a specific gravity centrifugal method or such.

In another embodiment, the present invention also provides pharmaceutical compositions that comprise a peptide of the present invention or a polynucleotide encoding the peptide for inducing an APC(s) having CTL-inducing ability.

Alternatively, the present invention further provides use of a peptide of the present invention or a polynucleotide encoding the peptide in the manufacture of a pharmaceutical composition for inducing an APC(s) having CTL-inducing ability.

Alternatively, the present invention further provides peptides of the present invention or polynucleotides encoding the peptides for use in the induction of an APC(s) having CTL-inducing ability.

Alternatively, the present invention further provides methods or processes of manufacturing a pharmaceutical composition for inducing an APC(s), wherein the method or process comprises a step of formulating a peptide of the present invention or a polynucleotide encoding the peptide with a pharmaceutically or physiologically acceptable carrier.

In another embodiment, the present invention further provides methods or processes of manufacturing a pharmaceutical composition for inducing an APC(s) having CTL-inducing ability, wherein the method or process comprises a step of mixing a peptide of the present invention or a polynucleotide encoding the peptide with a pharmaceutically or physiologically acceptable carrier.

APCs induced by the methods of the present invention can induce CTLs specific to CDCA1 (i.e., CTLs of the present invention).

(2) Methods of Inducing CTLs

The present invention also provides methods of inducing CTLs using peptides, polynucleotides, exosomes or APCs of the present invention.

When a peptide(s), a polynucleotide(s), an exosome(s) or an APC(s) of the present invention is administered to a subject, CTLs are induced in the body of the subject and the strength of the immune response targeting CDCA1-expressing cancer cells is enhanced.

Therefore, the methods of the present invention may comprise a step of administering a peptide(s), a polynucleotide(s), an APC(s) or an exosome(s) of the present invention to a subject.

Alternatively, CTLs can be induced by using them in vitro or ex vivo. For example, the methods of the present invention may include the following steps:
(a) collecting APCs from a subject;
(b) contacting the APCs of step (a) with a peptide of the present invention; and
(c) co-culturing the APCs of step (b) with CD8-positive T cells.

The induced CTLs may be returned to the subject afterwards.

The APCs to be co-cultured with the CD8-positive T cells in step (c) above can also be prepared by introducing into APCs a polynucleotide encoding a peptide of the present invention as described above in the "VI. Antigen-presenting cells (APCs)" section. However, the APCs to be used in the methods of the present invention are not limited thereto, and any APCs that present on their surface a complex of an HLA antigen and a peptide of the present invention can be used.

In the methods of the present invention, instead of such APCs, exosomes that present on their surface a complex of an HLA antigen and a peptide of the present invention can also be used. That is, the methods of the present invention can comprise a step of co-culturing with exosomes that present on their surface a complex of an HLA antigen and a peptide of the present invention. Such exosomes can be prepared by the above-described methods in the "V. Exosomes" section.

Further, CTLs can also be induced by introducing into a CD8-positive T cell a vector comprising a polynucleotide encoding each subunit of a TCR capable of binding to a peptide of the present invention presented by an HLA antigen on the cell surface. Such transformation can be carried out as described above in the "VIII. T cell receptors (TCRs)" section.

Accordingly, in one embodiment, the present invention provides methods of inducing CTLs, comprising a step selected from below:
(a) co-culturing CD8-positive T cells with APCs that present on their surface a complex of an HLA antigen and a peptide of present invention;
(b) co-culturing CD8-positive T cells with exosomes that present on their surface a complex of an HLA antigen and a peptide of present invention; and
(c) introducing into CD8-positive T cells, a vector comprising a polynucleotide encoding each subunit of a TCR capable of binding to a peptide of the present invention presented by an HLA antigen on a cell surface.

The above-described methods can be performed in vitro, ex vivo, or in vivo, and it is preferable to perform them in vitro or ex vivo. APCs or exosomes and CD8-positive T cells used in the above-described methods may be derived from a subject scheduled for administration of the induced CTLs, or they may be derived from a different subject. When APCs or exosomes and CD8-positive T cells derived from a subject (donor) different from the subject scheduled for administration are used, the subject of administration and the donor must have the identical HLA type. For example, when a peptide having the amino acid sequence selected from among SEQ ID NOs: 1, 8, 10, 13, 25, 33 to 35 and 37 or a modified peptide thereof is used as peptides of the present invention, the HLA type in both the subject of administration and the donor is preferably HLA-A01 (more preferably HLA-A*01:01). Alternatively, APCs or exosomes used in the above-described methods are preferably APCs or exosomes that present on their surface a complex of HLA-A01 (more preferably HLA-A*01:01) and a peptide of the present invention (a peptide having the amino acid sequence selected from among SEQ ID NOs: 1, 8, 10, 13, 25, 33 to 35 and 37 or a modified peptide thereof). In this case, the induced CTLs show a specific cytotoxic activity against cells that present a complex of HLA-A01 and a peptide of the present invention (for example, CDCA1-expressing HLA-A01-positive cells).

In another embodiment, the present invention also provides compositions or pharmaceutical compositions for inducing CTLs, comprising at least one active ingredient selected from below:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention also provides use of an active ingredient selected from below in the manufacture of compositions or pharmaceutical compositions for inducing CTLs:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

Alternatively, the present invention further provides an active ingredient selected from below for use in inducing CTLs:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

Alternatively, the present invention further provides a method or process for manufacturing a composition or pharmaceutical composition for inducing CTLs, which is a method or process that comprises a step of formulating an active ingredient selected from below with a pharmaceutically or physiologically acceptable carrier:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention further provides a method or process for manufacturing a composition or pharmaceutical composition for inducing CTLs, which is a method or process that comprises a step of mixing an active ingredient selected from below with a pharmaceutically or physiologically acceptable carrier:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

XI. Methods of Inducing an Immune Response

The present invention further provides methods of inducing an immune response against CDCA1-expressing cancers. Applicable cancers include bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue tumor, colon cancer and such, but are not limited thereto. It is preferable that the cancer expresses HLA-A01.

The present invention further provides methods of inducing an immune response against CDCA1-expressing cancer cells. CDCA1 is recognized to be overexpressed in various types of cancers described above. Thus, when an immune response against CDCA1-expressing cancer cells is induced, proliferation of the cancer cells is inhibited as a result. Accordingly, the present invention further provides methods of inhibiting proliferation of CDCA1-expressing cancer cells. The methods of the present invention are suitable, in particular, for inhibiting proliferation of cancer cells expressing CDCA1 and HLA-A01.

The methods of the present invention may comprise a step of administering a composition comprising any of the peptides of the present invention or a polynucleotide(s) encoding the peptide(s). The methods of the present invention also contemplate administration of APCs or exosomes presenting any of the peptides of the present invention. The details can be referred to the "IX. Pharmaceutical compositions" section, particularly portions describing regarding use of the pharmaceutical compositions of the present invention as vaccines. In addition, exosomes and APCs that can be used in the methods of the present invention for inducing an immune response are described in detail in "V. Exosomes", "VI. Antigen-presenting cells (APCs)" and in Items (1) and (2) of "X. Methods of using peptides, exosomes, APCs and CTLs" described above.

In another embodiment, the present invention provides pharmaceutical compositions or vaccines for inducing an immune response against cancers expressing CDCA1 and HLA-A01, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides pharmaceutical compositions or vaccines for inducing an immune response against cancer cells expressing CDCA1 and HLA-A01, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides pharmaceutical compositions or vaccines for inhibiting proliferation of cancer cells expressing CDCA1 and HLA-A01, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;

(d) an exosome that presents on its surface a peptide of the present invention; and
(e) a CTL of the present invention.

In another embodiment, the present invention provides use of an active ingredient selected from below in the manufacture of pharmaceutical compositions or vaccines for inducing an immune response against cancers expressing CDCA1 and HLA-A01:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides use of an active ingredient selected from below in the manufacture of pharmaceutical compositions or vaccines for inducing an immune response against cancer cells expressing CDCA1 and HLA-A01:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides use of an active ingredient selected from below in the manufacture of pharmaceutical compositions or vaccines for inhibiting proliferation of cancer cells expressing CDCA1 and HLA-A01:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

The present invention further provides methods or processes for manufacturing pharmaceutical compositions that induce an immune response against cancers expressing CDCA1 and HLA-A01, which is a method that may comprise a step of mixing or formulating a peptide of the present invention with a pharmaceutically acceptable carrier.

Alternatively, the present invention provides methods for inhibiting proliferation of cancer cells expressing CDCA1 and HLA-A01 in diseased sites of diseases mediated by angiogenesis or methods of inducing an immune response against cancers, which comprises a step of administering to a subject vaccines or pharmaceutical compositions comprising an active ingredient selected from below:
(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In the context of the present invention, cancers expressing CDCA1 and HLA-A01 can be treated by administering a peptide, a polynucleotide, an APC, an exosome and/or a CTL of the present invention. Alternatively, an immune response against CDCA1-expressing cancers can be induced by administering a peptide, a polynucleotide, an APC, an exosome and/or a CTL of the present invention. Examples of such cancers include bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue tumor, colon cancer and such, but are not limited thereto. Further, an immune response against cancer cells expressing CDCA1 and HLA-A01 can be induced by administering a peptide, a polynucleotide, an APC, an exosome and/or a CTL of the present invention. Therefore, before administering a vaccine or pharmaceutical composition comprising an active ingredient described above, it is preferable to confirm whether the level of CDCA1 expression at a diseased site in the subject to be treated is augmented or not. Similarly, it is also desirable to confirm that the subject to be treated is HLA-A01-positive. That is, in a preferred embodiment, the present invention can select a subject who is HLA-A01-positive and who has cancer expressing CDCA1 and administer the vaccine or the pharmaceutical composition of the present invention to the selected subject.

Thus, in one embodiment, the present invention provides a method of treating a cancer expressing CDCA1 and HLA-A01 in a patient in need of the cancer treatment, wherein the method comprises the steps below:
(i) measuring the level of CDCA1 expression in a biological sample collected from the diseased site of an HLA-A01-positive subject with cancer;
(ii) identifying a subject with CDCA1-expressing cancer based on the CDCA1 expression level measured in (i); and
(iii) administering to the subject with CDCA1-overexpressing cancer as compared to normal control at least one ingredient selected from the group consisting of (a) to (e) above.

Alternatively, the present invention further provides vaccines or pharmaceutical compositions comprising at least one active ingredient selected from the group consisting of (a) to (e) above for administration to an HLA-A01-positive subject with CDCA1-expressing cancer. The present invention further provides a method of identifying or selecting a subject to be treated with at least one active ingredient selected from the group consisting of (a) to (e) above, wherein the method comprises the steps below:
(i) measuring the level of CDCA1 expression in a biological sample collected from the diseased site of an HLA-A01-positive subject with cancer;
(ii) identifying a subject with CDCA1-expressing cancer based on the CDCA1 expression level measured in (i); and
(iii) identifying or selecting the subject identified in (ii) as a subject who may be treated with at least one active ingredient selected from the group consisting of (a) to (e) above.

Biological samples collected from a subject for measuring the CDCA1 expression level in the above-described methods are not particularly limited, and for example, tissue samples containing cancer cells collected by biopsy or such can be preferably used. The CDCA1 expression level in a biological sample can be measured by known methods, and for example, methods that detect transcription products of the CDCA1 gene by probes or PCR methods (for example, cDNA microarray method, Northern blot method, RT-PCR method or such), methods that detect translation products of the CDCA1 gene by antibodies or such (for example, Western blot method, immunostaining method or such), and such can be used. Further, biological samples may be blood samples, and in this case, the blood level of an antibody against CDCA1 is measured, and the CDCA1 expression level at a diseased site may be assessed based on the blood level. The blood level of an antibody against CDCA1 can be measured using known methods, and for example, enzyme immunoassay (EIA), enzyme-linked immunosorbent assay (ELISA), radioimmunoassay (RIA) and such using the CDCA1 protein or a peptide of the present invention as an antigen can be used. Alternatively, the CDCA1 expression level at a diseased site may be assessed by detecting CTLs specific to a peptide of the present invention. The CTL levels specific to a peptide of the present invention can be measured, for example, by separating PBMCs from the blood collected from a subject and measuring the cytotoxic activity against target cells pulsed with the peptide of the present invention. The cytotoxic activity can be measured, for example, by the amount of interferon-gamma release. Furthermore, complexes of the peptides of the present invention and HLA described below can also be used for measuring the CTL levels. Whether a subject's cancer expresses CDCA1 or not may be determined by comparing with the measurement results in a biological material of the same type collected from a subject without cancer. That is, if the level of a substance to be measured in a biological sample collected from a subject having cancer is elevated relative to the level in a biological material of the same type collected from another subject without cancer (normal control level), it can be determined that the cancer of the subject having cancer expresses CDCA1.

In a preferred embodiment, it is preferable to confirm the HLA type of a subject before administering at least one active ingredient selected from the group consisting of (a) to (e) above. For example, it is preferable to select an HLA-A01-positive subject as a subject to be administered with an active ingredient which is related to a peptide having the amino acid sequence selected from among SEQ ID NOs: 1, 8, 10, 13, 25, 33 to 35 and 37. The HLA of a subject can be confirmed by immunologically detecting an HLA on the surface of cells collected from the subject with an HLA-A01-specific antibody. Alternatively, the HLA of a subject can be determined by analyzing the genetic information of genomic DNA or mRNA obtained from cells collected from the subject. If a subject is HLA-A01-positive, then effective treatment can be expected in the present invention. In other words, a subject having homozygous or heterozygous HLA-A01 can be a target of administration.

The present invention further provides complexes of a peptide of the present invention and HLA. The complexes of the present invention described above may be monomers or multimers. When a complex of the present invention is a multimer, the number of polymerization is not particularly limited, and it can be a multimer of any number of polymerization. Examples include a tetramer, pentamer, hexamer and such, but are not limited thereto. The multimers of the present invention also encompass dextramers (WO2002/072631) and streptamers (Knabel M et al., Nat Med. 2002; 8(6): 631-7.). Complexes of a peptide of the present invention and HLA can be prepared according to known methods (for example, Altman J D et al., Science. 1996, 274(5284): 94-6; WO2002/072631; WO2009/003492; Knabel M et al., Nat Med. 2002; 8(6): 631-7, and such). The complexes of the present invention, for example, can be used in the quantification of CTLs specific to a peptide of the present invention. For example, a blood sample is collected from a subject administered with a pharmaceutical composition of the present invention, and CD4-negative cells are prepared after separation of PBMCs and contacted with a fluorescent dye-conjugated complex of the present invention. Then, the percentage of CTLs specific to a peptide of the present invention can be measured by flow cytometry analysis. For example, immune response-inducing effects by a pharmaceutical composition of the present invention can be monitored by measuring the specific CTLs against a peptide of the present invention before, during and/or after administration of the pharmaceutical composition of the present invention.

XII. Antibodies

The present invention further provides antibodies that bind to the peptide of the present invention. Preferable antibodies bind specifically to a peptide of the present invention, but do not bind (or weakly bind) to one that is not the peptide of the present invention. The binding specificity of an antibody can be confirmed by inhibition assay. That is, if the binding between an antibody to be analyzed and a full-length CDCA1 polypeptide is inhibited in the presence of a peptide of the present invention, this antibody is shown to specifically bind to the peptide of the present invention. Antibodies against peptides of the present invention can be used in assays of disease diagnosis and prognosis, as well as subject selection for administration of the pharmaceutical compositions of the present invention and monitoring of the pharmaceutical compositions of the present invention.

The present invention also provides various immunological assays for detecting and/or quantifying peptides of the present invention or fragments thereof. Such immunological assays include radioimmunoassay, immunochromatography, enzyme-linked immunosorbent assay (ELISA), enzyme-linked immunofluorescence assay (ELIFA) and such, without being limited thereto, and are performed within the scope of the various immunological assay formats well known in the art.

The antibodies of the present invention can be used in immunological imaging methods that can detect CDCA1-expressing diseases, and examples thereof include radioactive scintigraphic imaging using a labelled antibody of the present invention, without being limited thereto. Such assay methods are used clinically in the detection, monitoring, and prognosis of CDCA1-expressing cancers; and examples of such cancer include bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue tumor, colon cancer and such, without being limited thereto.

The antibodies of the present invention can be used in any arbitrary form such as monoclonal antibodies or polyclonal antibodies, and may further include anti-sera obtained by immunizing an animal such as a rabbit with a peptide of the present invention, all classes of polyclonal antibodies and monoclonal antibodies, human antibodies, as well as chimeric antibodies and humanized antibodies generated through gene recombination.

The peptide of the present invention or a fragment thereof used as an antigen for obtaining antibodies can be obtained by chemical synthesis or genetic engineering techniques based on the amino acid sequences disclosed herein.

The peptide used as an immunizing antigen may be a peptide of the present invention or a fragment of a peptide of the present invention. Further, the peptide may be bound to or conjugated with a carrier for increasing immunogenicity. Keyhole limpet hemocyanin (KLH) is well-known as a carrier. Methods for binding KLH to a peptide are also well known in the art.

Any mammal can be immunized with an antigen described above, and it is preferable to consider the compatibility with the parent cell used in cell fusion when generating a monoclonal antibody. Generally, animals of the order Rodentia, Lagomorpha or Primate can be used. Animals of the order Rodentia include, for example, mice, rats and hamsters. Animals of the order Lagomorpha include, for example, rabbits. Animals of the order Primate include, for example, Catarrhini monkeys (old world monkeys) such as cynomolgus monkey (*Macaca fascicularis*), rhesus monkeys, hamadryas, and chimpanzee.

Methods of immunizing animals with an antigen are known in the art. Intraperitoneal injection and subcutaneous injection of an antigen are standard methods for immunizing mammals. More specifically, an antigen is diluted and suspended in an appropriate amount of phosphate buffered saline (PBS), physiological saline, or such. As needed, an antigen suspension solution can be administered to mammals after being mixed with an appropriate amount of a standard adjuvant such as Freund's complete adjuvant and emulsified. Then, it is preferable to administer the antigen mixed with an appropriate amount of a Freund's incomplete adjuvant several times every 4 to 21 days. A suitable carrier may be used for immunization. After the above immunization, the serum can be examined by standard method with respect to increase in the quantity of the desired antibody.

Polyclonal antibodies against a peptide of the present invention can be prepared by collecting blood from mammals that have been confirmed with an increase in the serum level of the desired antibody after immunization, and separating the serum from blood by any conventional method. A polyclonal antibody may be a polyclonal antibody-containing serum, or a polyclonal antibody-containing fraction may be isolated from the serum. Immunoglobulin G or M can be prepared from fractions that recognize only a peptide of the present invention by, for example, using an affinity column conjugated with the peptide of the present invention, and then further purifying the fractions using a protein A or protein G column.

In order to prepare monoclonal antibodies, upon confirming an increase in the serum level of the desired antibody after immunization, immune cells are collected from the mammals and subjected to cell fusion. Immune cells used for cell fusion may be preferably obtained from the spleen. For the other parent cells fused with the above immune cells, for example, a mammalian myeloma cell, preferably a myeloma cell that has acquired a property for drug selection of fusion cells can be used.

The above immune cells can be fused with myeloma cells by following known methods, for example, the method of Milstein et al. (Galfre and Milstein, Methods Enzymol 73: 1981, 3-46).

Hybridomas obtained by cell fusion can be selected by culturing them in a standard selection medium such as the HAT medium (a medium containing hypoxanthine, aminopterin and thymidine). Cell culturing is typically continued in the HAT medium for a sufficient period of time (for example, several days to several weeks) to allow death of all other cells (non-fused cells) besides the desired hybridomas. Then, hybridoma cells producing the desired antibody can be screened and cloned by performing a standard limiting dilution.

In addition to the above methods of immunizing a non-human animal with an antigen for hybridoma preparation, human lymphocytes such as EB virus-infected lymphocytes can be immunized in vitro with a peptide, cells expressing the peptide, or lysates thereof. Then, the immunized lymphocytes can be fused with immortalized human-derived myeloma cells such as U266 to obtain hybridomas producing a desired human antibody capable of binding to the peptide (JPS63-17688).

Next, the obtained hybridoma is transplanted into the abdominal cavity of a mouse, and the ascites is extracted. The obtained monoclonal antibody can be purified by, for example, ammonium sulfate precipitation, protein A or protein G column, DEAE ion-exchange chromatography, or affinity column conjugated with the peptide of the present invention.

Alternatively, antibody-producing immune cells such as the immunized lymphocytes can be immortalized by a cancer gene and used for the preparation of monoclonal antibodies.

The monoclonal antibodies obtained as such can also be prepared by recombination using genetic engineering techniques (see, e.g., Borrebaeck and Larrick, Therapeutic Monoclonal Antibodies published in United Kingdom by MacMillan Publishers LTD (1990)). For example, an antibody-encoding DNA can be cloned from immune cells such as antibody-producing hybridoma or immunized lymphocytes and inserted into a suitable vector, and then this is introduced into host cells to prepare a recombinant antibody. The present invention also provides recombinant antibodies prepared as described above.

Further, the antibodies of the present invention may be antibody fragments or modified antibodies, as long as they bind to the peptides of the present invention. For example, the antibody fragments may be Fab, $F(ab')_2$, Fv, or a single chain Fv (scFv) in which Fv fragments derived from an H chain and an L chain are linked with a suitable linker (Huston et al., Proc Natl Acad Sci USA 1988, 85: 5879-83). More specifically, antibody fragments may be generated by treating an antibody with an enzyme such as papain or pepsin. Alternatively, a gene encoding an antibody fragment may be constructed, inserted into an expression vector, and expressed in an appropriate host cell (see, e.g., Co et al., J Immunol 1994, 152: 2968-76; Better and Horwitz, Methods Enzymol 1989, 178: 476-96; Pluckthun and Skerra, Methods Enzymol 1989, 178: 497-515; Lamoyi, Methods Enzymol 1986, 121: 652-63; Rousseaux et al., Methods Enzymol 1986, 121: 663-9; Bird and Walker, Trends Biotechnol 1991, 9: 132-7).

Antibodies may be modified by conjugation with various molecules such as polyethyleneglycol (PEG). The present invention provides such modified antibodies. Modified antibodies can be obtained by chemically modifying the antibodies. These modification methods are conventional in the art.

Alternatively, the antibodies of the present invention can be obtained as chimeric antibodies of a non-human antibody-derived variable region and a human antibody-derived constant region, or as humanized antibodies comprising a non-human antibody-derived complementarity determining region (CDR) and a human antibody-derived framework region (FR) and constant region. Such antibodies can be prepared according to known techniques. Humanization can be carried out by substituting a human antibody sequence(s) with a corresponding non-human antibody CDR sequence(s) (see, e.g., Verhoeyen et al., Science 1988, 239: 1534-6). Thus, such humanized antibodies are chimeric antibodies in which the substantially less than an intact human variable domain has been substituted with a corresponding sequence from a non-human species.

Intact human antibodies comprising a human variable region in addition to the human framework and constant regions can also be used. Such antibodies can be generated using various techniques known in the art. For example, in vitro methods include use of recombinant libraries of human antibody fragments presented on bacteriophages (for example, Hoogenboom & Winter, J. Mol. Biol. 1991, 227: 381). Similarly, human antibodies can also be generated by introducing human immunoglobulin gene loci into transgenic animals, for example, mice, in which the endogenous immunoglobulin genes have been partially or completely inactivated. This approach is described in, for example, U.S. Pat. Nos. 6,150,584, 5,545,807, 5,545,806, 5,569,825, 5,625,126, 5,633,425 and 5,661,016.

Antibodies obtained as described above may be purified to homogeneity. For example, antibody separation and purification can be performed according to separation methods and purification methods used for general proteins. For example, an antibody can be separated and isolated by appropriately selecting and combining use of column chromatographies such as affinity chromatography, filter, ultrafiltration, salting-out, dialysis, SDS-polyacrylamide gel electrophoresis and isoelectric focusing electrophoresis (Antibodies: A Laboratory Manual. Ed Harlow and David Lane, Cold Spring Harbor Laboratory (1988)), but are not limited thereto.

Protein A column and protein G column can be used as the affinity column. Exemplary protein A columns to be used include, for example, Hyper D, POROS and Sepharose F. F. (Pharmacia). Besides affinity chromatography, exemplary chromatography includes, for example, ion-exchange chromatography, hydrophobic chromatography, gel filtration, reversed-phase chromatography, adsorption chromatography and such (Strategies for Protein Purification and Characterization: A Laboratory Course Manual. Ed Daniel R. Marshak et al., Cold Spring Harbor Laboratory Press (1996)). The chromatography procedures can be carried out by liquid-phase chromatography such as HPLC and FPLC.

The antigen-binding activity of an antibody of the present invention can be measured, for example, by using absorbance measurement, enzyme-linked immunosorbent assay (ELISA), enzyme immunoassay (EIA), radioimmunoassay (RIA), and/or immunofluorescence (IF). In the case of ELISA, an antibody of the present invention is immobilized onto a plate, a peptide of the present invention is applied to the plate, and then a sample containing the desired antibody, such as culture supernatant of antibody-producing cells or purified antibodies, is applied. Next, a secondary antibody that recognizes the primary antibody and is labelled with an enzyme such as alkaline phosphatase is applied and the plate is incubated. Then, after washing, an enzyme substrate such as p-nitrophenyl phosphate is applied to the plate, and the antigen-binding activity of the sample is evaluated by measuring absorbance. To assess the binding activity of an antibody, peptide fragments such as C-terminal or N-terminal fragments may be used as an antigen. BIAcore (Pharmacia) may be used to evaluate the activity of an antibody of the present invention.

It is possible to detect or measure a peptide of the present invention using the above methods, by exposing an antibody of the present invention to a sample assumed to contain the peptide of the present invention, and detecting or measuring an immune complex formed between the antibody and the peptide.

For example, an antibody of the present invention can be used to detect a peptide of the present invention present in the blood sample (for example, serum sample) of a subject. Alternatively, an antibody of the present invention present in the blood sample (for example, serum sample) of a subject can also be detected using a peptide of the present invention. The result of measuring a peptide of the present invention or an antibody of the present invention in the blood sample of a subject can be utilized to the subject selection for administration of the pharmaceutical compositions of the present invention or monitoring of the efficacy of the pharmaceutical compositions of the present invention.

XIII. Vectors and Host Cells

The present invention provides vectors comprising a polynucleotide encoding a peptide of the present invention and host cells introduced with the vectors. A vector of the present invention may be used to keep a polynucleotide of the present invention in a host cell, to express a peptide of the present invention in a host cell, or to administer a polynucleotide of the present invention for gene therapy.

When E. coli is a host cell and a vector is amplified and produced in a large amount in E. coli (for example, JM109, DH5-alpha, HB101 or XL1-Blue), the vector needs to have a "replication origin" for amplification in E. coli and a marker gene for selection of transformed E. coli (for example, a drug resistance gene selected by a drug such as ampicillin, tetracycline, kanamycin, chloramphenicol). For example, the M13-series vectors, pUC-series vectors, pBR322, pBluescript, pCR-Script and such can be used. In addition, pGEM-T, pDIRECT and pT7 can be used for cloning as well as the above vectors. When a vector is used in the production of a peptide of the present invention, an expression vector can be used. For example, an expression vector for expression in E. coli needs to have the above features for amplification in E. coli. When E. coli such as JM109, DH5-alpha, HB101 or XL1-Blue are used as a host cell, the vector needs to have a promoter, for example, lacZ promoter (Ward et al., Nature 1989, 341: 544-6; FASEB J. 1989, 6: 2422-7), araB promoter (Better et al., Science 1988, 240: 1041-3), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may contain a signal sequence for peptide secretion. An exemplary signal sequence that directs the peptide to be secreted to the periplasm of the E. coli is the pelB signal sequence (Lei et al., J Bacteriol. 1987, 169: 4379). Means for introducing the vectors into the target host cells include, for example, the calcium chloride method and the electroporation method.

In addition to E. coli, for example, expression vectors derived from mammals (for example, pcDNA3 (Invitrogen) and pEGF-BOS (Nucleic Acids Res 1990, 18(17): 5322), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vectors derived from yeast (e.g., "Pichia Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells such as CHO, COS or NIH3T3 cells, the vector needs to carry a promoter necessary for expression in such cells, for example, the SV40 promoter (Mulligan et al., Nature 1979, 277: 108), the MMLV-LTR promoter, the EF1-alpha promoter (Mizushima et al., Nucleic Acids Res. 1990, 18: 5322), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The embodiments of the present invention are exemplified below based on the above explanation; however, the present invention is not limited to these embodiments.

[1] A peptide of less than 15 amino acids having cytotoxic T cell (CTL)-inducing ability, which comprises the amino acid sequence selected from the group of:
  (a) the amino acid sequence selected from the group consisting of SEQ ID NOs: 1, 8, 10, 13, 25, 33 to 35 and 37; and
  (b) the amino acid sequence in which one, two, three or several amino acids are substituted, deleted, inserted and/or added to the amino acid sequence selected from the group consisting of SEQ ID NOs: 1, 8, 10, 13, 25, 33 to 35 and 37.

[2] The peptide of [1], comprising the amino acid sequence in which one or more (i.e., one, two or three) substitution(s) selected from (a) to (c) below is introduced into the amino acid sequence selected from the group consisting of SEQ ID NOs: 1, 8, 10, 13, 25, 33 to 35 and 37:
  (a) the second amino acid from the N terminus is substituted with an amino acid selected from the group consisting of threonine and serine;
  (b) the third amino acid from the N terminus is substituted with an amino acid selected from the group consisting of aspartic acid and glutamic acid; and
  (c) the C-terminal amino acid is substituted with tyrosine.

[3] The peptide of [1], which consists of the amino acid sequence selected from the group consisting of SEQ ID NOs: 1, 8, 10, 13, 25, 33 to 35 and 37.

[4] A polynucleotide, which encodes the peptide of any one of [1] to [3].

[5] A composition comprising a pharmaceutically acceptable carrier and at least one ingredient selected from the group consisting of (a) to (e) below:
  (a) one or more types of peptides of any one of [1] to [3];
  (b) one or more types of polynucleotides encoding the peptide(s) of any one of [1] to [3] in an expressible form;
  (c) an antigen-presenting cell (APC) that presents on its cell surface a complex of the peptide of any one of [1] to [3] and an HLA antigen;
  (d) an exosome that presents on its cell surface a complex of the peptide of any one of [1] to [3] and an HLA antigen; and
  (e) a CTL that targets the peptide of any one of [1] to [3].

[6] The composition of [5], which is a composition for inducing a CTL(s), wherein the ingredient is at least one ingredient selected from the group consisting of (a) to (d) below:
  (a) one or more types of peptides of any one of [1] to [3];
  (b) one or more types of polynucleotides encoding the peptide(s) of any one of [1] to [3] in an expressible form;
  (c) an antigen-presenting cell (APC) that presents on its cell surface a complex of the peptide of any one of [1] to [3] and an HLA antigen; and
  (d) an exosome that presents on its cell surface a complex of the peptide of any one of [1] to [3] and an HLA antigen.

[7] The composition of [5], which is a pharmaceutical composition.

[8] The composition of [7], which is a pharmaceutical composition for one or more uses selected from the group consisting of (i) cancer treatment, (ii) cancer prevention (prophylaxis) and (iii) prevention (prophylaxis) of postoperative cancer recurrence.

[9] The composition of [7], which is for inducing an immune response against cancer.

[10] The composition of [8] or [9], wherein the cancer is selected from the group consisting of bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue tumor and colon cancer.

[11] The composition of any one of [5] to [10], which is formulated for administration to a subject positive for HLA-A01.

[12] A method of inducing an APC(s) having CTL-inducing ability, which comprises a step selected from the group consisting of:
  (a) contacting an APC(s) with the peptide of any one of [1] to [3] in vitro, ex vivo or in vivo; and
  (b) introducing a polynucleotide encoding the peptide of any one of [1] to [3] into an APC(s).

[13] A method of inducing a CTL(s), which comprises a step selected from the group consisting of (a) to (c) below:
  (a) co-culturing a CD8-positive T cell(s) with an APC(s) that presents on its surface a complex of an HLA antigen and the peptide of any one of [1] to [3];
  (b) co-culturing a CD8-positive T cell(s) with an exosome(s) that presents on its surface a complex of an HLA antigen and the peptide of any one of [1] to [3]; and
  (c) introducing into a CD8-positive T cell(s) a polynucleotide encoding each subunit of a T cell receptor (TCR) capable of binding to the peptide of any one of [1] to [3] presented by an HLA antigen on a cell surface.

[14] An APC that presents on its surface a complex of an HLA antigen and the peptide of any one of [1] to [3].

[15] The APC of [14], which is induced by the method of [12].

[16] A CTL that targets the peptide of any one of [1] to [3].

[17] The CTL of [16], which is induced by the method of [13].

[18] A method of inducing an immune response against cancer, which comprises administering to a subject at least one ingredient selected from the group consisting of (a) to (e) below:
   (a) one or more types of peptides of any one of [1] to [3];
   (b) one or more types of polynucleotides encoding the peptide(s) of any one of [1] to [3] in an expressible form;
   (c) an antigen-presenting cell (APC) that presents on its cell surface a complex of the peptide of any one of [1] to [3] and an HLA antigen;
   (d) an exosome that presents on its cell surface a complex of the peptide of any one of [1] to [3] and an HLA antigen; and
   (e) a CTL that targets the peptide of any one of [1] to [3].

[19] A method of treating and/or preventing cancer, and/or preventing postoperative recurrence thereof, which comprises administering to a subject at least one ingredient selected from the group consisting of (a) to (e) below:
   (a) one or more types of peptides of any one of [1] to [3];
   (b) one or more types of polynucleotides encoding the peptide(s) of any one of [1] to [3] in an expressible form;
   (c) an antigen-presenting cell (APC) that presents on its cell surface a complex of the peptide of any one of [1] to [3] and an HLA antigen;
   (d) an exosome that presents on its cell surface a complex of the peptide of any one of [1] to [3] and an HLA antigen; and
   (e) a CTL that targets the peptide of any one of [1] to [3].

[20] An antibody that binds to the peptide of any one of [1] to [3].

[21] A method of screening for a peptide having CTL-inducing ability, which comprises the steps of
   (a) generating candidate sequences consisting of an amino acid sequence in which one, two or several amino acid residues are substituted, deleted, inserted and/or added to an original amino acid sequence consisting of the amino acid sequence selected from among SEQ ID NOs: 1, 8, 10, 13, 25, 33 to 35 and 37;
   (b) selecting from among the candidate sequences generated in (a), a candidate sequence that does not have significant homology (sequence identity) with any known human gene product other than CDCA1;
   (c) contacting an APC(s) with a peptide consisting of the candidate sequence selected in (b);
   (d) contacting the APC(s) of (c) with a CD8-positive T cell(s); and
   (e) selecting a peptide having an equal to or higher CTL-inducing ability than that of a peptide consisting of the original amino acid sequence.

[22] Use of at least one active ingredient selected from the group consisting of (a) to (e) below in the manufacture of a composition for inducing an immune response against cancer:
   (a) one or more types of peptides of any one of [1] to [3];
   (b) one or more types of polynucleotides encoding the peptide(s) of any one of [1] to [3] in an expressible form;
   (c) an antigen-presenting cell (APC) that presents on its cell surface a complex of the peptide of any one of [1] to [3] and an HLA antigen;
   (d) an exosome that presents on its cell surface a complex of the peptide of any one of [1] to [3] and an HLA antigen; and
   (e) a CTL that targets the peptide of any one of [1] to [3].

[23] Use of at least one ingredient selected from the group consisting of (a) to (e) below in the manufacture of a pharmaceutical composition for treating and/or preventing cancer, and/or preventing postoperative recurrence thereof:
   (a) one or more types of peptides of any one of [1] to [3];
   (b) one or more types of polynucleotides encoding the peptide(s) of any one of [1] to [3] in an expressible form;
   (c) an antigen-presenting cell (APC) that presents on its cell surface a complex of the peptide of any one of [1] to [3] and an HLA antigen;
   (d) an exosome that presents on its cell surface a complex of the peptide of any one of [1] to [3] and an HLA antigen; and
   (e) a CTL that targets the peptide of any one of [1] to [3].

[24] Use of at least one ingredient selected from the group consisting of (a) to (e) below for inducing an immune response against cancer:
   (a) one or more types of peptides of any one of [1] to [3];
   (b) one or more types of polynucleotides encoding the peptide(s) of any one of [1] to [3] in an expressible form;
   (c) an antigen-presenting cell (APC) that presents on its cell surface a complex of the peptide of any one of [1] to [3] and an HLA antigen;
   (d) an exosome that presents on its cell surface a complex of the peptide of any one of [1] to [3] and an HLA antigen; and
   (e) a CTL that targets the peptide of any one of [1] to [3].

[25] Use of at least one ingredient selected from the group consisting of (a) to (e) below for treating and/or preventing cancer and/or preventing postoperative recurrence thereof:
   (a) one or more types of peptides of any one of [1] to [3];
   (b) one or more types of polynucleotides encoding the peptide(s) of any one of [1] to [3] in an expressible form;
   (c) an antigen-presenting cell (APC) that presents on its cell surface a complex of the peptide of any one of [1] to [3] and an HLA antigen;
   (d) an exosome that presents on its cell surface a complex of the peptide of any one of [1] to [3] and an HLA antigen; and
   (e) a CTL that targets the peptide of any one of [1] to [4].

[26] A method of inducing cytotoxic activity against a CDCA1-expressing cell(s), which comprises a step of administering to a subject at least one ingredient selected from the group consisting of (a) to (e) below:
   (a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[27] A freeze-dried formulation comprising one or more types of peptides of any one of [1] to [3].

[28] A pharmaceutical composition, which is prepared by a method that comprises dissolving one or more types of peptides of any one of [1] to [3] in a water-soluble carrier, and performing filtration sterilization.

[29] A filtration-sterilized aqueous solution, which is an aqueous solution that comprises one or more types of peptides of any one of [1] to [3] and a water-soluble carrier.

[30] An emulsion comprising one or more types of peptides of any one of [1] to [3], a water-soluble carrier and an oil adjuvant.

[31] A kit comprising a container that houses the composition of any one of [5] to [11] and a container that stores an adjuvant.

[32] A kit comprising a container that stores a freeze-dried formulation comprising the peptide of any one of [1] to [3], a container that stores an adjuvant, and a container that stores a re-dissolving solution for the freeze-dried formulation.

Preferably, the kit of the present invention further comprises an HLA-A01 detection reagent additionally.

The present invention is explained herein in detail with reference to its specific embodiments. However, it should be understood that the above explanation is in fact an illustrative and explanatory explanation, and is intended to explain the present invention and preferred embodiments thereof. Through routine experimentation, one skilled in the art will readily recognize that various changes and modifications can be made therein without departing from the spirit and scope of the present invention. Thus, the present invention is not confined to the above explanation, but is intended to be defined by the appended claims and equivalents thereto.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

EXAMPLES

Materials and Methods

Cell Lines

C1R, an HLA-A- and HLA-B-negative human B lymphoblastoid cell line, and COS7, an African green monkey kidney cell line, were purchased from ATCC.

Generation of Target Cells with Constitutive HLA-A*01:01 Expression

C1R cells (C1R-A01) that constitutively express HLA-A*01:01 was used as cells for stimulating CTLs. A cDNA encoding the HLA-A*01:01 gene was amplified by PCR and introduced into an expression vector. C1R cells incorporated with HLA-A*01:01 gene expression vector were cultured for two weeks under drug selection with a medium containing G418 (Invitrogen). After diluting G418-resistant C1R cell suspension, the cells were seeded into a 96-well plate, and subjected to selective culture for another 30 days with a medium containing G418. The HLA-A*01:01 expression in C1R cells was verified by flow cytometric analysis.

Selection of CDCA1-Derived Peptides

CDCA1-derived 8mer, 9mer and 10mer peptides that are expected to bind to HLA-A*01:01 were determined using the binding prediction server "NetMHC 3.2" (www.cbs.dtu.dk/services/NetMHC-3.2/) (Buus et al., Tissue Antigens. 2003, 62(5): 378-84; Nielsen et al., Protein Sci. 2003, 12(5): 1007-17; Lundegaard C et al., Bioinformatics. 2008, 24(11): 1397-98), "BIMAS" (www-bimas.cit.nih.gov/molbio/hla bind/) (Parker K C et al., J Immunol 1994, 152(1): 163-75) and "SYFPEITHI" (www.syfpeithi.de/bin/MHCServer.dll/EpitopePrediction.htm) (Rammensee H G et al., Immunogenetics 1999, 50(3-4): 213-9).

Peptide Synthesis

The peptides were chemically synthesized by American Peptide Company (Sunnyvale, CA) according to a standard solid-phase synthesis method, and purified by reversed phase high-performance liquid chromatography (HPLC). The quality (purity of 90% or higher) of the peptides was guaranteed by HPLC and mass spectrometry. The peptides were dissolved in dimethylsulfoxide (final concentration: 20 mg/ml) and stored at −80 degrees C.

In Vitro CTL Induction

Monocyte-derived dendritic cells (DCs) were used as the antigen-presenting cell to induce a cytotoxic T lymphocyte (CTL) specific to peptides presented on human leukocyte antigens (HLAs). DCs were prepared in vitro as already reported in the literature (Nakahara S et al., Cancer Res 2003, 63(14): 4112-8). Specifically, peripheral-blood mononuclear cells (PBMCs) collected from healthy volunteers (HLA-A*01:01-positive) with the Ficoll-Paque plus solution (Pharmacia) were seeded into plastic tissue culture dishes (Corning) to allow attachment of monocytes in PBMCs to the dishes. Then, the cells were cultured in the presence of 1000 IU/ml granulocyte macrophage colony-stimulating factor (R&D System) and 1000 IU/ml interleukin (IL)-4 (R&D System) for seven days. As medium, an AIM-V medium (Invitrogen) containing inactivated AB type serum (MP Biomedicals) was used (2% ABS/AIM-V medium). DCs induced to differentiate from monocytes by cytokines were pulsed with 20 micro-g/ml each of the synthesized peptides (37 degrees C., for three hours). Peptide pulsing was performed in the AIM-V medium. These peptide-pulsed DCs were inactivated by X-ray irradiation (20 Gy), and mixed in a 1:20 ratio with autologous CD8-positive T cells obtained by using the CD8 Positive Isolation Kit (Invitrogen) ($1.5 \times 10^4$ DCs and $3 \times 10^5$ CD8-positive T cells), and cultured in a 48-well plate (Corning). The volume of 2% ABS/AIM-V medium was 0.5 ml per 1 well, and IL-7 (R&D System) was added (final concentration: 10 ng/ml) to the well. Two days after the start of culture, IL-2 (Novartis) was added thereto (final concentration: 20 IU/ml). On $7^{th}$ day of culture and $14^{th}$ day of culture, CD8-positive T cells were further stimulated with peptide-pulsed DCs. The DCs were prepared before use by the same method as above. On $21^{st}$ day or thereafter (after the third DC stimulation), IFN-gamma production of CD8-positive T cells against peptide-pulsed C1R-A01 was confirmed by enzyme-linked immunospot (ELISPOT) assay (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

CTL Proliferation Procedure

CTLs were propagated using a method similar to that reported by Riddell et al. (Walter E A et al., N Engl J Med 1995, 333(16): 1038-44; Riddell S R et al., Nat Med 1996, 2(2): 216-23). In a flask for tissue culture (FALCON), the CTLs were cultured in 5% ABS/AIM-V medium (culture solution volume: 25 ml/flask) with two types of human B lymphoblastoid cell lines ($5 \times 10^6$ cells each) treated with mitomycin C and anti-CD3 antibody (BD biosciences, final concentration: 40 ng/ml). On the next day after the culturing was started, IL-2 was added to the culture (IL-2 final concentration: 120 IU/ml). On days 5, 8, and 11, the medium was changed to 5% ABS/AIM-V medium containing 60 IU/ml IL-2 (IL-2 final concentration: 30 IU/ml) (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Establishment of CTL Clones (Limiting Dilution Method)

After CTLs were induced in vitro, the CTLs were seeded at 1 cell/well or 10 cells/well in a 96-well round-bottomed microplate (Corning). The CTLs were cultured in 5% ABS/AIM-V medium (culture solution volume: 150 ml/well) with two types of human B lymphoblastoid cell lines ($1 \times 10^4$ cells each) treated with mitomycin C, anti-CD3 antibody (final concentration: 30 ng/ml), and IL-2 (final concentration: 125 IU/ml). After 10 days, 50 ml of 5% ABS/AIM-V medium containing 500 IU/ml IL-2 was added to the culture. After $14^{th}$ day, CTLs that showed peptide-specific IFN-gamma production in the ELISPOT assay were propagated by the method mentioned above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Confirmation of IFN-Gamma Production

The IFN-gamma ELISPOT assay and IFN-gamma ELISA were performed to confirm peptide-specific IFN-gamma production of CTLs induced by a peptide. C1R-A01 pulsed with a peptide was prepared as target cells. The IFN-gamma ELISPOT assay and IFN-gamma ELISA were performed according to the procedures recommended by the assay kit manufacturer.

Establishment of Target Cells in which CDCA1 and HLA-A*01:01 were Forcibly Expressed The cDNA encoding the CDCA1 or HLA-A*01:01 gene were amplified by PCR. Each PCR amplified product was incorporated into an expression vector. Using Lipofectamine 2000 (Invitrogen), either or both of the CDCA1 gene expression vector and the HLA-A*01:01 gene expression vector were introduced into COS7 cells, an HLA-negative cell line, according to the procedure recommended by the manufacturer. On the next day of the gene introduction, the COS7 cells were separated using Versene (Invitrogen) and used as target cells.

Results

Selection of HLA-A*01:01 Binding Peptides Derived from CDCA1

Table 1a, Table 1b, and Table 1c show 8mer, 9mer, and 10mer peptides derived from CDCA1 that were predicted to bind to HLA-A*01:01 by "NetMHC 3.2" in descending order of binding affinity, respectively. Table 2a and Table 2b show 9mer and 10mer peptides derived from CDCA1 that were predicted to bind to HLA-A*01:01 by "BIMAS" in descending order of binding score. Table 3a and Table 3b show 9mer and 10mer peptides derived from CDCA1 that were predicted to bind to HLA-A*01:01 by "SYFPEITHI" in descending order of binding score. The number of Start Position in each table indicates the position of the first amino acid of the peptide when counted from the N-terminus of the CDCA1 protein. Thirty-nine peptides in total potentially having HLA-A*01:01 binding ability became epitope peptide candidates.

TABLE 1a

CDCA1-derived 8mer peptide predicted to bind to HLA-A*01:01 by NetMHC3.2

| Start Position | Amino Acid Sequence | Affinity (nM) | SEQ ID NO: |
|---|---|---|---|
| 138 | YMEFLWQY | 50 | 1 |

TABLE 1b

CDCA1-derived 9mer peptides predicted to bind to HLA-A*01:01 by NetMHC3.2

| Start Position | Amino Acid Sequence | Affinity (nM) | SEQ ID NO: |
|---|---|---|---|
| 183 | LSDGIQELQ | 2488 | 2 |
| 49 | YMRALQIVY | 2570 | 3 |
| 325 | ESDESELKK | 3358 | 4 |
| 303 | LSDNREKLA | 6648 | 5 |
| 57 | YGIRLEHFY | 6700 | 6 |
| 380 | VQEKRGAVY | 8200 | 7 |

TABLE 1c

CDCA1-derived 10mer peptides predicted to bind to HLA-A*01:01 by NetMHC3.2

| Start Position | Amino Acid Sequence | Affinity (nM) | SEQ ID NO: |
|---|---|---|---|
| 136 | ETYMEFLWQY | 92 | 8 |
| 66 | MMPVNSEVMY | 455 | 9 |
| 56 | VYGIRLEHFY | 1040 | 10 |
| 121 | LSGIINFIHF | 2410 | 11 |
| 287 | PSCQLEVQLY | 2630 | 12 |
| 48 | IYMRALQIVY | 2933 | 13 |
| 325 | ESDESELKKL | 4331 | 14 |
| 436 | GIEKAAEDSY | 4636 | 15 |
| 379 | KVQEKRGAVY | 4867 | 16 |
| 129 | HFREACRETY | 7569 | 17 |
| 335 | KTEENSFKRL | 8751 | 18 |
| 424 | LNLKTALEKY | 9039 | 19 |

TABLE 1c -continued

CDCA1-derived 10mer peptides predicted to bind to HLA-A*01:01 by NetMHC3.2

| Start Position | Amino Acid Sequence | Affinity (nM) | SEQ ID NO: |
|---|---|---|---|
| 451 | KTAELKRKMF | 9261 | 20 |
| 146 | KSSADKMQQL | 9961 | 21 |

TABLE 2a

CDCA1-derived 9mer peptides predicted to bind to HLA-A*01:01 by BIMAS

| Start Position | Amino Acid Sequence | Score | SEQ ID NO: |
|---|---|---|---|
| 335 | KTEENSFKR | 112.5 | 22 |
| 41 | KPEVLHMIY | 56.25 | 23 |
| 25 | GADGKNLTK | 50 | 24 |
| 290 | QLVQLYQK | 36 | 25 |
| 244 | IVDSPEKLK | 10 | 26 |

TABLE 2b

CDCA1-derived 10mer peptides predicted to bind to HLA-A*01:01 by BIMAS

| Start Position | Amino Acid Sequence | Score | SEQ ID NO: |
|---|---|---|---|
| 452 | TAELKRKMFK | 90 | 27 |
| 91 | HLDSFLPICR | 25 | 28 |
| 323 | QIESDESELK | 18 | 29 |
| 290 | QLEVQLYQKK | 18 | 30 |
| 447 | KIDEKTAELK | 10 | 31 |
| 106 | TADILCPKAK | 10 | 32 |

TABLE 3a

CDCA1-derived 9mer peptides predicted to bind to HLA-A*01:01 by SYFPEITHI

| Start Position | Amino Acid Sequence | Score | SEQ ID NO: |
|---|---|---|---|
| 130 | FREACRETY | 24 | 33 |
| 246 | DSPEKLKNY | 19 | 34 |
| 268 | ARQEVVEKY | 18 | 35 |
| 1 | METLSFPRY | 18 | 36 |
| 288 | SCQLEVQLY | 18 | 37 |

TABLE 3b

CDCA1-derived 10mer peptides predicted to bind to HLA-A*01:01 by SYFPEITHI

| Start Position | Amino Acid Sequence | Score | SEQ ID NO: |
|---|---|---|---|
| 303 | LSDNREKLAS | 18 | 38 |
| 245 | VDSPEKLKNY | 18 | 39 |

CTL induction by HLA-A*01:01-restricted CDCA1-derived peptides

Figure 1:
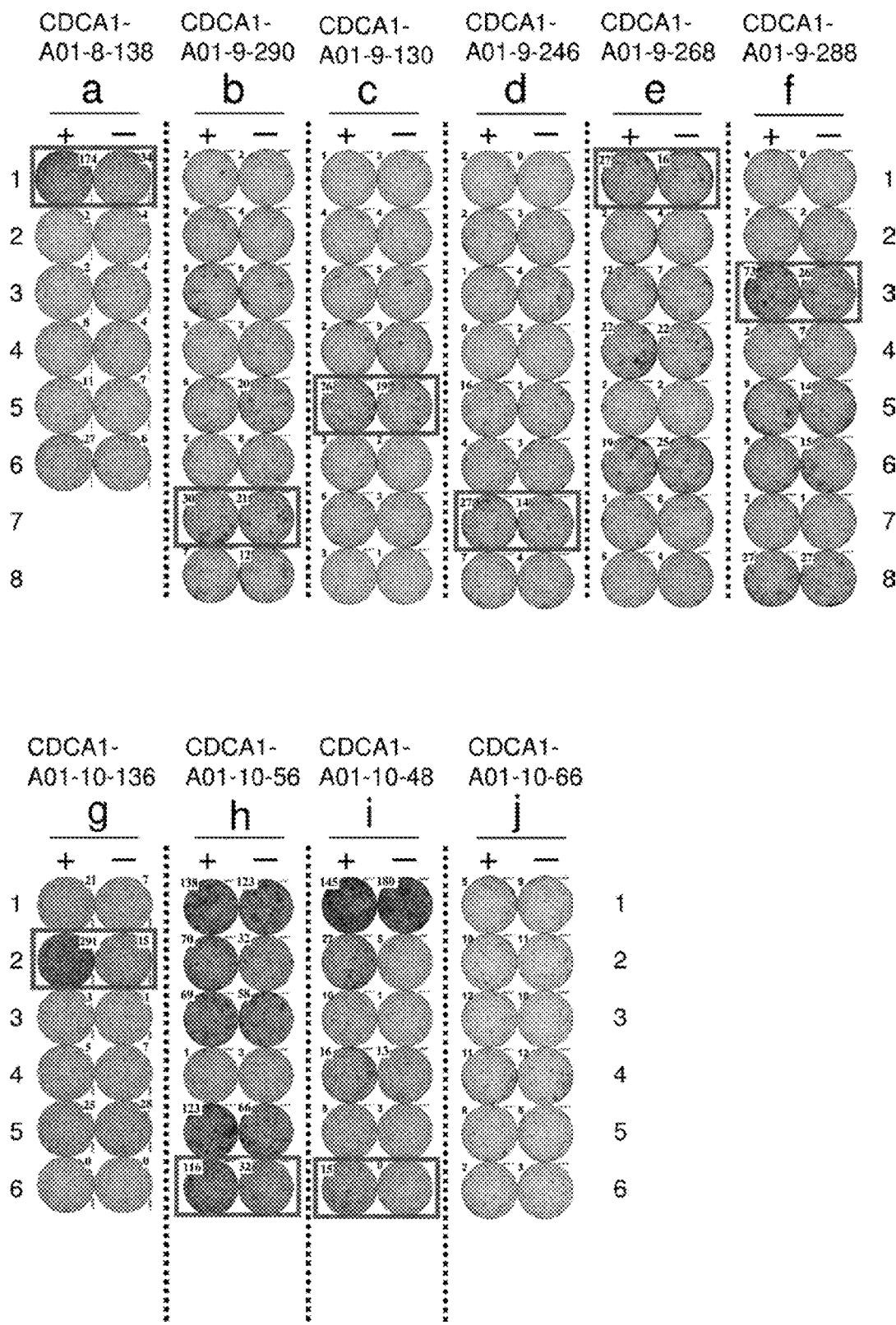
FIG. 1 is comprised of photos (a) to (j) showing the results of the IFN-gamma enzyme-linked immunospot (ELISPOT)

CTLs specific to peptides derived from CDCA1 were induced according to the protocol described in "Materials and Methods." Peptide-specific IFN-gamma production was measured by the IFN-gamma ELISPOT assay (FIG. 1). Peptide-specific IFN-gamma production relative to the control well was observed in:

Well #1 with CDCA1-A01-8-138 (SEQ ID NO: 1) (a),
Well #7 with CDCA1-A01-9-290 (SEQ ID NO: 25) (b),
Well #5 with CDCA1-A01-9-130 (SEQ ID NO: 33) (c),
Well #7 with CDCA1-A01-9-246 (SEQ ID NO: 34) (d),
Well #1 with CDCA1-A01-9-268 (SEQ ID NO: 35) (e),
Well #3 with CDCA1-A01-9-288 (SEQ ID NO: 37) (f),
Well #2 with CDCA1-A01-10-136 (SEQ ID NO: 8) (g),
Well #6 with CDCA1-A01-10-56 (SEQ ID NO: 10) (h), and
Well #6 with CDCA1-A01-10-48 (SEQ ID NO: 13) (i).

Meanwhile, no IFN-gamma production specific to other peptides shown in Table 1b, Table 1c, Table 2a, Table 2b, Table 3a, and Table 3b was observed. No IFN-gamma production specific to CDCA1-A01-10-66 (SEQ ID NO: 9), an example of typical negative data, was observed (j). Every peptide was likely to bind to HLA-A*01:01, but the nine peptides derived from CDCA1 were selected as peptides having strong CTL-inducing ability consequently.

Establishment of CTL Clones Specific to CDCA1-Derived HLA-A*01:01-Restricted Peptides By limiting dilution method, CTL clones were established from cells in Well #2 which showed IFN-gamma production specific to CDCA1-A01-10-136 (SEQ ID NO: 8) (FIG. 1 photo g), Well #6 which showed IFN-gamma production specific to CDCA1-A01-10-56 (SEQ ID NO: 10) (FIG. 1 photo h), and Well #6 which showed IFN-gamma production specific to CDCA1-A01-10-48 (SEQ ID NO: 13) (FIG. 1 photo i) in the IFN-gamma ELISPOT assay. As a result of IFN-gamma measurement by ELISA, CTL clones stimulated by CDCA1-A01-10-136 (SEQ ID NO: 8), CDCA1-A01-10-56 (SEQ ID NO: 10), or CDCA1-A01-10-48 (SEQ ID NO: 13) showed peptide-specific IFN-gamma production (FIG. 2).

IFN-Gamma Production of CTLs Against Target Cells Expressing CDCA1 and HLA-A*01:01

IFN-gamma production of CTL clones specific to CDCA1-A01-10-136 (SEQ ID NO: 8) against target cells expressing CDCA1 and HLA-A*01:01 was verified. COS7 cells expressing both CDCA1 and HLA-A*01:01 were prepared as target cells. COS7 cells expressing either CDCA1 or HLA-A*01:01 were prepared as negative control cells. CTL clones specific to CDCA1-A01-10-136 (SEQ ID NO: 8) showed IFN-gamma production against COS7 cells expressing both CDCA1 and HLA-A*01:01 (FIG. 3). By contrast, no significant IFN-gamma production was observed against negative control cells. From the above, it was clearly demonstrated that CDCA1-A01-10-136 (SEQ ID NO: 8) is a peptide produced by antigen processing and is presented on the cell surface together with the HLA-A01 molecule and recognized by CTLs. The result suggests that CDCA1-A01-10-136 (SEQ ID NO: 8) is useful as a cancer vaccine targeting cancer patients with elevated CDCA1 expression.

Homology Analysis of Antigen Peptides

It was confirmed that CDCA1-A01-8-138 (SEQ ID NO: 1), CDCA1-A01-9-290 (SEQ ID NO: 25), CDCA1-A01-9-130 (SEQ ID NO: 33), CDCA1-A01-9-246 (SEQ ID NO: 34), CDCA1-A01-9-268 (SEQ ID NO: 35), CDCA1-A01-9-288 (SEQ ID NO: 37), CDCA1-A01-10-136 (SEQ ID NO: 8), CDCA1-A01-10-56 (SEQ ID NO: 10), and CDCA1-A01-10-48 (SEQ ID NO: 13) were able to induce CTLs that showed peptide-specific IFN-gamma production. Thus, in order to confirm that the sequences of CDCA1-A01-8-138 (SEQ ID NO: 1), CDCA1-A01-9-290 (SEQ ID NO: 25), CDCA1-A01-9-130 (SEQ ID NO: 33), CDCA1-A01-9-246 (SEQ ID NO: 34), CDCA1-A01-9-268 (SEQ ID NO: 35), CDCA1-A01-9-288 (SEQ ID NO: 37), CDCA1-A01-10-136 (SEQ ID NO: 8), CDCA1-A01-10-56 (SEQ ID NO: 10), and CDCA1-A01-10-48 (SEQ ID NO: 13) are derived only from CDCA1, the homology analysis of the peptide sequences was performed using the BLAST algorithm (blast.ncbi.nlm.nih.gov/Blast.cgi). The result shows that the sequences of CDCA1-A01-8-138 (SEQ ID NO: 1), CDCA1-A01-9-290 (SEQ ID NO: 25), CDCA1-A01-9-130 (SEQ ID NO: 33), CDCA1-A01-9-246 (SEQ ID NO: 34), CDCA1-A01-9-268 (SEQ ID NO: 35), CDCA1-A01-9-288 (SEQ ID NO: 37), CDCA1-A01-10-136 (SEQ ID NO: 8), CDCA1-A01-10-56 (SEQ ID NO: 10), and CDCA1-A01-10-48 (SEQ ID NO: 13) were observed only in CDCA1. Therefore, to the best of the present inventors' knowledge, these peptides are unique to CDCA1 and considered to have little possibility of eliciting an unintended immune response against molecules other than CDCA1 that are already known to sensitize the human immune system. In conclusion, novel HLA-A*01:01-restrictive epitope peptides derived from CDCA1 were identified and shown to be applicable to cancer immunotherapy.

INDUSTRIAL APPLICABILITY

The present invention provides CDCA1-derived novel HLA-A01-restricted epitope peptides that induce a potent and specific anti-tumor immune response and thus have applicability for a wide range of cancer types. The peptides, compositions, APCs, and CTLs in the present invention can be used as a peptide vaccine for cancer expressing CDCA1, for example, bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue tumor, and colon cancer.

While the present invention is herein described in detail and with respect to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

SEQUENCE LISTING

```
Sequence total quantity: 48
SEQ ID NO: 1              moltype = AA  length = 8
FEATURE                   Location/Qualifiers
REGION                    1..8
                          note = a peptide derived from CDCA1
source                    1..8
                          mol_type = protein
                          organism = synthetic construct
SEQUENCE: 1
YMEFLWQY                                                                  8

SEQ ID NO: 2              moltype = AA  length = 9
FEATURE                   Location/Qualifiers
REGION                    1..9
                          note = a peptide derived from CDCA1
source                    1..9
                          mol_type = protein
                          organism = synthetic construct
SEQUENCE: 2
LSDGIQELQ                                                                 9

SEQ ID NO: 3              moltype = AA  length = 9
FEATURE                   Location/Qualifiers
REGION                    1..9
                          note = a peptide derived from CDCA1
source                    1..9
                          mol_type = protein
                          organism = synthetic construct
SEQUENCE: 3
YMRALQIVY                                                                 9

SEQ ID NO: 4              moltype = AA  length = 9
FEATURE                   Location/Qualifiers
REGION                    1..9
                          note = a peptide derived from CDCA1
source                    1..9
                          mol_type = protein
```

-continued

```
                          organism = synthetic construct
SEQUENCE: 4
ESDESELKK                                                                   9

SEQ ID NO: 5              moltype = AA  length = 9
FEATURE                   Location/Qualifiers
REGION                    1..9
                          note = a peptide derived from CDCA1
source                    1..9
                          mol_type = protein
                          organism = synthetic construct
SEQUENCE: 5
LSDNREKLA                                                                   9

SEQ ID NO: 6              moltype = AA  length = 9
FEATURE                   Location/Qualifiers
REGION                    1..9
                          note = a peptide derived from CDCA1
source                    1..9
                          mol_type = protein
                          organism = synthetic construct
SEQUENCE: 6
YGIRLEHFY                                                                   9

SEQ ID NO: 7              moltype = AA  length = 9
FEATURE                   Location/Qualifiers
REGION                    1..9
                          note = a peptide derived from CDCA1
source                    1..9
                          mol_type = protein
                          organism = synthetic construct
SEQUENCE: 7
VQEKRGAVY                                                                   9

SEQ ID NO: 8              moltype = AA  length = 10
FEATURE                   Location/Qualifiers
REGION                    1..10
                          note = a peptide derived from CDCA1
source                    1..10
                          mol_type = protein
                          organism = synthetic construct
SEQUENCE: 8
ETYMEFLWQY                                                                  10

SEQ ID NO: 9              moltype = AA  length = 10
FEATURE                   Location/Qualifiers
REGION                    1..10
                          note = a peptide derived from CDCA1
source                    1..10
                          mol_type = protein
                          organism = synthetic construct
SEQUENCE: 9
MMPVNSEVMY                                                                  10

SEQ ID NO: 10             moltype = AA  length = 10
FEATURE                   Location/Qualifiers
REGION                    1..10
                          note = a peptide derived from CDCA1
source                    1..10
                          mol_type = protein
                          organism = synthetic construct
SEQUENCE: 10
VYGIRLEHFY                                                                  10

SEQ ID NO: 11             moltype = AA  length = 10
FEATURE                   Location/Qualifiers
REGION                    1..10
                          note = a peptide derived from CDCA1
source                    1..10
                          mol_type = protein
                          organism = synthetic construct
SEQUENCE: 11
LSGIINFIHF                                                                  10

SEQ ID NO: 12             moltype = AA  length = 10
FEATURE                   Location/Qualifiers
REGION                    1..10
                          note = a peptide derived from CDCA1
source                    1..10
```

```
                        mol_type = protein
                        organism = synthetic construct
SEQUENCE: 12
PSCQLEVQLY                                                                      10

SEQ ID NO: 13           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 13
IYMRALQIVY                                                                      10

SEQ ID NO: 14           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 14
ESDESELKKL                                                                      10

SEQ ID NO: 15           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 15
GIEKAAEDSY                                                                      10

SEQ ID NO: 16           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 16
KVQEKRGAVY                                                                      10

SEQ ID NO: 17           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 17
HFREACRETY                                                                      10

SEQ ID NO: 18           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 18
KTEENSFKRL                                                                      10

SEQ ID NO: 19           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 19
LNLKTALEKY                                                                      10

SEQ ID NO: 20           moltype = AA  length = 10
FEATURE                 Location/Qualifiers
REGION                  1..10
                        note = a peptide derived from CDCA1
```

```
source                   1..10
                         mol_type = protein
                         organism = synthetic construct
SEQUENCE: 20
KTAELKRKMF                                                                    10

SEQ ID NO: 21            moltype = AA   length = 10
FEATURE                  Location/Qualifiers
REGION                   1..10
                         note = a peptide derived from CDCA1
source                   1..10
                         mol_type = protein
                         organism = synthetic construct
SEQUENCE: 21
KSSADKMQQL                                                                    10

SEQ ID NO: 22            moltype = AA   length = 9
FEATURE                  Location/Qualifiers
REGION                   1..9
                         note = a peptide derived from CDCA1
source                   1..9
                         mol_type = protein
                         organism = synthetic construct
SEQUENCE: 22
KTEENSFKR                                                                     9

SEQ ID NO: 23            moltype = AA   length = 9
FEATURE                  Location/Qualifiers
REGION                   1..9
                         note = a peptide derived from CDCA1
source                   1..9
                         mol_type = protein
                         organism = synthetic construct
SEQUENCE: 23
KPEVLHMIY                                                                     9

SEQ ID NO: 24            moltype = AA   length = 9
FEATURE                  Location/Qualifiers
REGION                   1..9
                         note = a peptide derived from CDCA1
source                   1..9
                         mol_type = protein
                         organism = synthetic construct
SEQUENCE: 24
GADGKNLTK                                                                     9

SEQ ID NO: 25            moltype = AA   length = 9
FEATURE                  Location/Qualifiers
REGION                   1..9
                         note = a peptide derived from CDCA1
source                   1..9
                         mol_type = protein
                         organism = synthetic construct
SEQUENCE: 25
QLEVQLYQK                                                                     9

SEQ ID NO: 26            moltype = AA   length = 9
FEATURE                  Location/Qualifiers
REGION                   1..9
                         note = a peptide derived from CDCA1
source                   1..9
                         mol_type = protein
                         organism = synthetic construct
SEQUENCE: 26
IVDSPEKLK                                                                     9

SEQ ID NO: 27            moltype = AA   length = 10
FEATURE                  Location/Qualifiers
REGION                   1..10
                         note = a peptide derived from CDCA1
source                   1..10
                         mol_type = protein
                         organism = synthetic construct
SEQUENCE: 27
TAELKRKMFK                                                                    10

SEQ ID NO: 28            moltype = AA   length = 10
FEATURE                  Location/Qualifiers
REGION                   1..10
```

```
                        note = a peptide derived from CDCA1
source                  1..10
                        mol_type = protein
                        organism = synthetic construct
SEQUENCE: 28
HLDSFLPICR                                                              10

SEQ ID NO: 29           moltype = AA   length = 10
FEATURE                 Location/Qualifiers
REGION                  1..10
                        note = a peptide derived from CDCA1
source                  1..10
                        mol_type = protein
                        organism = synthetic construct
SEQUENCE: 29
QIESDESELK                                                              10

SEQ ID NO: 30           moltype = AA   length = 10
FEATURE                 Location/Qualifiers
REGION                  1..10
                        note = a peptide derived from CDCA1
source                  1..10
                        mol_type = protein
                        organism = synthetic construct
SEQUENCE: 30
QLEVQLYQKK                                                              10

SEQ ID NO: 31           moltype = AA   length = 10
FEATURE                 Location/Qualifiers
REGION                  1..10
                        note = a peptide derived from CDCA1
source                  1..10
                        mol_type = protein
                        organism = synthetic construct
SEQUENCE: 31
KIDEKTAELK                                                              10

SEQ ID NO: 32           moltype = AA   length = 10
FEATURE                 Location/Qualifiers
REGION                  1..10
                        note = a peptide derived from CDCA1
source                  1..10
                        mol_type = protein
                        organism = synthetic construct
SEQUENCE: 32
TADILCPKAK                                                              10

SEQ ID NO: 33           moltype = AA   length = 9
FEATURE                 Location/Qualifiers
REGION                  1..9
                        note = a peptide derived from CDCA1
source                  1..9
                        mol_type = protein
                        organism = synthetic construct
SEQUENCE: 33
FREACRETY                                                                9

SEQ ID NO: 34           moltype = AA   length = 9
FEATURE                 Location/Qualifiers
REGION                  1..9
                        note = a peptide derived from CDCA1
source                  1..9
                        mol_type = protein
                        organism = synthetic construct
SEQUENCE: 34
DSPEKLKNY                                                                9

SEQ ID NO: 35           moltype = AA   length = 9
FEATURE                 Location/Qualifiers
REGION                  1..9
                        note = a peptide derived from CDCA1
source                  1..9
                        mol_type = protein
                        organism = synthetic construct
SEQUENCE: 35
ARQEVVEKY                                                                9

SEQ ID NO: 36           moltype = AA   length = 9
FEATURE                 Location/Qualifiers
```

```
REGION                  1..9
                        note = a peptide derived from CDCA1
source                  1..9
                        mol_type = protein
                        organism = synthetic construct
SEQUENCE: 36
METLSFPRY                                                              9

SEQ ID NO: 37           moltype = AA  length = 9
FEATURE                 Location/Qualifiers
REGION                  1..9
                        note = a peptide derived from CDCA1
source                  1..9
                        mol_type = protein
                        organism = synthetic construct
SEQUENCE: 37
SCQLEVQLY                                                              9

SEQ ID NO: 38           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 38
LSDNREKLAS                                                            10

SEQ ID NO: 39           moltype = AA  length = 10
FEATURE                 Location/Qualifiers
REGION                  1..10
                        note = a peptide derived from CDCA1
source                  1..10
                        mol_type = protein
                        organism = synthetic construct
SEQUENCE: 39
VDSPEKLKNY                                                            10

SEQ ID NO: 40           moltype = DNA  length = 22
FEATURE                 Location/Qualifiers
misc_feature            1..22
                        note = a PCR primer for the TCR analysis
source                  1..22
                        mol_type = other DNA
                        organism = synthetic construct
SEQUENCE: 40
gtctaccagg cattcgcttc at                                              22

SEQ ID NO: 41           moltype = DNA  length = 24
FEATURE                 Location/Qualifiers
misc_feature            1..24
                        note = a PCR primer for the TCR analysis
source                  1..24
                        mol_type = other DNA
                        organism = synthetic construct
SEQUENCE: 41
tcagctggac cacagccgca gcgt                                            24

SEQ ID NO: 42           moltype = DNA  length = 21
FEATURE                 Location/Qualifiers
misc_feature            1..21
                        note = a PCR primer for the TCR analysis
source                  1..21
                        mol_type = other DNA
                        organism = synthetic construct
SEQUENCE: 42
tcagaaatcc tttctcttga c                                               21

SEQ ID NO: 43           moltype = DNA  length = 24
FEATURE                 Location/Qualifiers
misc_feature            1..24
                        note = a PCR primer for the TCR analysis
source                  1..24
                        mol_type = other DNA
                        organism = synthetic construct
SEQUENCE: 43
ctagcctctg gaatcctttc tctt                                            24

SEQ ID NO: 44           moltype = DNA  length = 1989
```

```
FEATURE                 Location/Qualifiers
source                  1..1989
                        mol_type = unassigned DNA
                        organism = Homo sapiens
CDS                     301..1695
                        protein_id = 45
                        translation = METLSFPRYNVAEIVIHIRNKILTGADGKNLTKNDLYPNPKPEVLH
                        MIYMRALQIVYGIRLEHFYMMPVNSEVMYPHLMEGFLPFSNLVTHLDSFLPICRVNDFE
                        TADILCPKAKRTSRFLSGIINFIHFREACRETYMEFLWQYKSSADKMQQLNAAHQEALM
                        KLERLDSVPVEEQEEFKQLSDGIQELQQSLNQDFHQKTIVLQEGNSQKKSNISEKTKRL
                        NELKLSVVSLKEIQESLKTKIVDSPEKLKNYKEKMKDTVQKLKNARQEVVEKYEIYGDS
                        VDCLPSCQLEVQLYQKKIQDLSDNREKLASILKESLNLEDQIESDESELKKLKTEENSF
                        KRLMIVKKEKLATAQFKINKKHEDVKQYKRTVIEDCNKVQEKRGAVYERVTTINQEIQK
                        IKLGIQQLKDAAEREKLKSQEIFLNLKTALEKYHDGIEKAAEDSYAKIDEKTAELKRKM
                        FKMST
SEQUENCE: 44
gcggaatggg gcgggacttc cagtaggagg cggcaagttt gaaaagtgat gacggttgac    60
gtttgctgat ttttgacttt gcttgtagct gctccccgaa ctcgccgtct tcctgtcggc   120
ggccggcact gtaggtgagc gcgagaggac ggaggaagga agcctgcaga cagacgcctt   180
ctccatccca aggcgcgggc aggtgccggg acgctgggcc tggcggtgtt ttcgtcgtgc   240
tcagcggtgg gaggaggcgg aagaaaccag agcctggaga attaacagga aacttccaag   300
atggaaactt tgtctttccc cagatataat gtagctgaaa ttgtgattca tattcgcaat   360
aagatcttaa caggagctga tggtaaaaac ctcaccaaga atgatcttta tccaaatcca   420
aagcctgaag tcttgcacat gatctacatg agagccttac aaatagtata tggaattcga   480
ctggaacatt tttacatgat gccagtgaac tctgaagtca tgtatccaca tttaatggaa   540
ggcttcttac cattcagcaa tttagttact catctggact cattttttgcc tatctgccgg   600
gtgaatgact ttgagactgc tgatattcta tgtccaaaag caaaacggac aagtcggttt   660
ttaagtggca ttatcaactt tattcacttc agagaagcat gccgtgaaac gtatatggaa   720
tttctttggc aatataaatc ctctgcggac aaaatgcaac agttaaacgc cgcacaccag   780
gaggcattaa tgaaactgga gacttgat tctgttccga ttgaagagca agaagagttc   840
aagcagcttt cagatggaat tcaggagcta caacaatcac taaatcagga ttttcatcaa   900
aaaacgatag tgctgcaaga gggaaattcc caaaagaagt caaatatttc agagaaaacc   960
aagcgtttga tgaactaaa attgtcggtg gttctttga agaaatacaa gagagtttg    1020
aaaacaaaaa ttgtggattc tccagagaag ttaaagaatt ataaagaaaa aatgaaagat  1080
acggtccaga agcttaaaaa tgccagacaa gaagtggtgg agaaatatga aatctatgga  1140
gactcagttg actgcctgcc ttcatgtcag ttggaagtgc agttatatca aaagaaaata  1200
caggaccttt cagataatag ggaaaaatta gccagtatct taaggagag cctgaacttg  1260
gaggaccaaa ttgagagtga tgagtcagaa ctgaagaaat tgaagactaa agaaaattcg  1320
ttcaaaagac tgatgattgt gaagaaggaa aaacttgcca cagcacaatt caaaataaat  1380
aagaagcatg aagatgttaa gcaatacaaa cgcacagtaa ttgaggattg caataaagtt  1440
caagaaaaaa gaggtgctgt ctatgaacga gtaaccacaa ttaatcaaga aatccaaaaa  1500
attaaacttg gaattcaaca actaaagat gctgctgaaa gggagaaact gaagtcccag  1560
gaaatatttc taaacttgaa aactgctttg gagaaatacc acgacggtat tgaaaaggca  1620
gcagaggact cctatgctaa gatagatgag aagacagctg aactgaagag gaagatgttc  1680
aaaatgtcaa cctgattaac aaaattacat gtctttttgt aaatggcttg ccatctttta  1740
atttttctatt tagaaagaaa agttgaagcg aatgaagta tcagaagtac caaataatgt  1800
tggcttcatc agtttttata cactctcata agtagttaat aagtgaatt taatgtaggc  1860
ttttattaat ttataattaa aataacttgt gcagctattc atgtctctac tctgcccctt  1920
gttgtaaata gtttgagtaa aacaaaacta gttaccttttg aaatatatat attttttcct  1980
gttactatc                                                          1989

SEQ ID NO: 45            moltype = AA  length = 464
FEATURE                  Location/Qualifiers
source                   1..464
                         mol_type = protein
                         organism = Homo sapiens
SEQUENCE: 45
METLSFPRYN VAEIVIHIRN KILTGADGKN LTKNDLYPNP KPEVLHMIYM RALQIVYGIR    60
LEHFYMMPVN SEVMYPHLME GFLPFSNLVT HLDSFLPICR VNDFETADIL CPKAKRTSRF   120
LSGIINFIHF REACRETYME FLWQYKSSAD KMQQLNAAHQ EALMKLERLD SVPVEEQEEF   180
KQLSDGIQEL QQSLNQDFHQ KTIVLQEGNS QKKSNISEKT KRLNELKLSV VSLKEIQESL   240
KTKIVDSPEK LKNYKEKMKD TVQKLKNARQ EVVEKYEIYG DSVDCLPSCQ LEVQLYQKKI   300
QDLSDNREKL ASILKESLNL EDQIESDESE LKKLKTEENSF KRLMIVKKE KLATAQFKIN   360
KKHEDVKQYK RTVIEDCNKV QEKRGAVYER VTTINQEIQK IKLGIQQLKD AAEREKLKSQ   420
EIFLNLKTAL EKYHDGIEKA AEDSYAKIDE KTAELKRKMF KMST                   464

SEQ ID NO: 46            moltype = DNA  length = 1843
FEATURE                  Location/Qualifiers
source                   1..1843
                         mol_type = unassigned DNA
                         organism = Homo sapiens
CDS                      155..1549
                         protein_id = 47
                         translation = METLSFPRYNVAEIVIHIRNKILTGADGKNLTKNDLYPNPKPEVLH
                         MIYMRALQIVYGIRLEHFYMMPVNSEVMYPHLMEGFLPFSNLVTHLDSFLPICRVNDFE
                         TADILCPKAKRTSRFLSGIINFIHFREACRETYMEFLWQYKSSADKMQQLNAAHQEALM
                         KLERLDSVPVEEQEEFKQLSDGIQELQQSLNQDFHQKTIVLQEGNSQKKSNISEKTKRL
                         NELKLSVVSLKEIQESLKTKIVDSPEKLKNYKEKMKDTVQKLKNARQEVVEKYEIYGDS
                         VDCLPSCQLEVQLYQKKIQDLSDNREKLASILKESLNLEDQIESDESELKKLKTEENSF
```

```
                        KRLMIVKKEKLATAQFKINKKHEDVKQYKRTVIEDCNKVQEKRGAVYERVTTINQEIQK
                        IKLGIQQLKDAAEREKLKSQEIFLNLKTALEKYHDGIEKAAEDSYAKIDEKTAELKRKM
                        FKMST
SEQUENCE: 46
gcggaatggg gcgggacttc cagtaggagg cggcaagttt gaaaagtgat gacggttgac   60
gtttgctgat tttgacttt gcttgtagct gctccccgaa ctcgccgtct tcctgtcggc  120
ggccggcact gtagattaac aggaaacttc caagatggaa actttgtctt tccccagata  180
taatgtagct gagattgtga ttcatattcg caataagatc ttaacaggag ctgatggtaa  240
aaacctcacc aagaatgatc tttatccaaa tccaaagcct gaagtcttgc acatgatcta  300
catgagagcc ttacaaatag tatatggaat tcgactggaa cattttaca tgatgccagt   360
gaactctgaa gtcatgtatc cacatttaat ggaaggcttc ttaccattca gcaatttagt  420
tactcatctg gactcatttt tgcctatctg ccgggtgaat gactttgaga ctgctgatat  480
tctatgtcca aaagcaaaac ggacaagtcg gttttaagt ggcattatca actttattca   540
cttcagagaa gcatgccgtg aaacgtatat ggaatttctt tggcaatata aatcctctgc  600
ggacaaaatg caacagttaa acgccgcaca ccaggaggca ttaatgaaac tggagagact  660
tgattctgtt ccagttgaag agcaagaaga gttcaagcag ctttcagatg gaattcagga  720
gctacaacaa tcactaaatc aggattttca tcaaaaaacg atagtgctgc aagagggaaa  780
ttcccaaaag aagtcaaata tttcagagaa aaccaagcgt ttgaatgaac taaaattgtc  840
ggtggtttct ttgaaagaaa tacaagagag tttgaaaaca aaaattgtgg attctccaga  900
gaagttaaag aattataaag aaaaaatgaa agatacggtc cagaagctta aaaatgccag  960
acaagaagtg gtggagaaat atgaaatcta tggagactca gttgactgcc tgccttcatg  1020
tcagttggaa gtgcagttat atcaaaagaa aatacaggac ctttcagata ataggggaaa  1080
attagccagt atcttaaagg agagcctgaa cttggaggac caaattgaga gtgatgagtc  1140
agaactgaag aaattgaaga ctgaagaaaa ttcgttcaaa agactgatga ttgtgaagaa  1200
ggaaaaactt gccacagcac aattcaaaat aaataagaag catgaagatg ttaagcaata  1260
caaacgcaca gtaattgagg atgcaataa agttcaagaa aaaagaggtg ctgtctatga   1320
acgagtaacc acaattaatc aagaaatcca aaaaattaaa cttggaattc aacaactaaa  1380
agatgctgct gaaagggaga aactgaagtc ccaggaaata tttctaaact tgaaaactgc  1440
tttggagaaa taccacgacg gtattgaaaa ggcagcagag gactcctatg ctaagataga  1500
tgagaagaca gctgaactga agaggaagat gttcaaaatg tcaacctgat taacaaaatt  1560
acatgtcttt ttgtaaatgg cttgccatct tttaattttc tatttagaaa gaaaagttga  1620
agcgaatgga agtatcagaa gtaccaaata atgttggctt catcagtttt tatacactct  1680
cataagtagt taataagatg aatttaatgt aggcttttat taatttataa ttaaaataac  1740
ttgtgcagct attcatgtct ctactctgcc ccttgttgta aatagtttga gtaaaacaaa  1800
actagttacc tttgaaatat atatatttt ttctgttact atc                     1843

SEQ ID NO: 47           moltype = AA  length = 464
FEATURE                 Location/Qualifiers
source                  1..464
                        mol_type = protein
                        organism = Homo sapiens
SEQUENCE: 47
METLSFPRYN VAEIVIHIRN KILTGADGKN LTKNDLYPNP KPEVLHMIYM RALQIVYGIR   60
LEHFYMMPVN SEVMYPHLME GFLPFSNLVT HLDSFLPICR VNDFETADIL CPKAKRTSRF  120
LSGIINFIHF REACRETYME FLWQYKSSAD KMQQLNAAHQ EALMKLERLD SVPVEEQEEF  180
KQLSDGIQEL QQSLNQDFHQ KTIVLQEGNS QKKSNISEKT KRLNELKLSV VSLKEIQESL  240
KTKIVDSPEK LKNYKEKMKD TVQKLKNARQ EVVEKYEIYG DSVDCLPSCQ LEVQLYQKKI  300
QDLSDNREKL ASILKESLNL EDQIESDESE LKKLKTEENS FKRLMIVKKE KLATAQFKIN  360
KKHEDVKQYK RTVIEDCNKV QEKRGAVYER VTTINQEIQK IKLGIQQLKD AAEREKLKSQ  420
EIFLNLKTAL EKYHDGIEKA AEDSYAKIDE KTAELKRKMF KMST                   464

SEQ ID NO: 48           moltype = AA  length = 4
FEATURE                 Location/Qualifiers
REGION                  1..4
                        note = a linker peptide
source                  1..4
                        mol_type = protein
                        organism = synthetic construct
SEQUENCE: 48
NKRK                                                                 4
```

The invention claimed is:

1. A method of treating cancer and/or preventing postoperative recurrence thereof in a subject having a homozygous positive for-HLA-A01, which comprises administering to the subject at least one ingredient selected from the group consisting of (a) to (e) below:

(a) one or more types of peptides;

(b) one or more types of polynucleotides encoding one or more types of peptides in an expressible form;

(c) an antigen-presenting cell (APC) that presents on its cell surface a complex of a peptide and an HLA;

(d) an exosome that presents on its cell surface a complex of a peptide; and (e) a CTL that targets a peptide;

wherein the peptide or each of the one or more types of peptides is a CDCA1-derived HLA-A01-restricted peptide having cytotoxic T cell (CTL)-inducing ability, which consists of the amino acid sequence selected from the group consisting of SEQ ID NOs: 1, 8, 10, 13, 25, 33 to 35 and 37.

2. A method of treating a cancer expressing CDCA1 and HLA-A01 in a subject having a homozygous HLA-A01 in need of the cancer treatment, wherein the method comprises the steps below:

(i) measuring the level of CDCA1 expression in a biological sample collected from the diseased site of a subject with cancer;

(ii) identifying a subject with CDCA1-overexpressing cancer based on the CDCA1 expression level measured in (i); and
(iii) administering to the subject with CDCA1-overexpressing cancer as compared to normal control at least one ingredient selected from the group consisting of (a) to (e) below:
(a) one or more types of peptides;
(b) one or more types of polynucleotides encoding one or more types of peptides in an expressible form;
(c) an antigen-presenting cell (APC) that presents on its cell surface a complex of a peptide and an HLA;
(d) an exosome that presents on its cell surface a complex of a peptide; and
(e) a CTL that targets a peptide;
wherein the peptide or each of the one or more types of peptides is a CDCA1-derived HLA-A01-restricted peptide having cytotoxic T cell (CTL)-inducing ability, which consists of the amino acid sequence selected from the group consisting of SEQ ID NOs: 1, 8, 10, 13, 25, 33 to 35 and 37.

3. A method of inducing an immune response against cancer in a subject having a homozygous HLA-A01 in need of the cancer treatment, which comprises administering to the subject at least one ingredient selected from the group consisting of (a) to (e) below:
(a) one or more types of peptides;
(b) one or more types of polynucleotides encoding one or more types of peptides in an expressible form;
(c) an antigen-presenting cell (APC) that presents on its cell surface a complex of a peptide and an HLA;
(d) an exosome that presents on its cell surface a complex of a peptide; and
(e) a CTL that targets a peptide;
wherein the peptide or each of the one or more types of peptides is a CDCA1-derived HLA-A01-restricted peptide having cytotoxic T cell (CTL)-inducing ability, which consists of the amino acid sequence selected from the group consisting of SEQ ID NOs: 1, 8, 10, 13, 25, 33 to 35 and 37.

4. The method of claim 1, wherein the cancer is selected from the group consisting of bladder cancer, breast cancer, cervical cancer, cholangiocellular cancer, chronic myeloid leukemia (CML), esophagus cancer, gastric cancer, non-small-cell lung cancer, lymphoma, osteosarcoma, prostate cancer, kidney cancer, small-cell lung cancer, head and neck cancer, soft tissue cancer, and colon cancer.

5. The method of claim 1, wherein the method further comprises a step for selecting a subject having a homozygous HLA-A01, prior to administering the ingredient.

6. The method of claim 1, wherein the ingredient is the one or more types of peptides.

7. The method of claim 6, wherein the one or more types of peptides is administered in combination with an adjuvant in an amount to enhance an immune response.

8. The method of claim 1, wherein administering to the subject the at least one ingredient induces CTL in an HLA-A01 restrictive manner.

9. The method of claim 2, wherein administering to the subject the at least one ingredient induces CTL in an HLA-A01 restrictive manner.

10. The method of claim 3, wherein the immune response against cancer is induced in an HLA-A01 restrictive manner.

* * * * *

UNITED STATES PATENT AND TRADEMARK OFFICE
CERTIFICATE OF CORRECTION

| | |
|---|---|
| PATENT NO. | : 12,195,559 B2 |
| APPLICATION NO. | : 18/094167 |
| DATED | : January 14, 2025 |
| INVENTOR(S) | : Sachiko Yamashita and Tetsuro Hikichi |

Page 1 of 1

It is certified that error appears in the above-identified patent and that said Letters Patent is hereby corrected as shown below:

In the Claims

Column 67, Claim 1, Line 57: Delete "positive for-".

Signed and Sealed this
Eighteenth Day of March, 2025

Coke Morgan Stewart
*Acting Director of the United States Patent and Trademark Office*